United States Patent
Kodama et al.

(10) Patent No.: US 10,864,516 B2
(45) Date of Patent: Dec. 15, 2020

(54) DISPENSING DEVICE AND LIQUID TRANSFER METHOD

(71) Applicant: FUJIFILM CORPORATION, Tokyo (JP)

(72) Inventors: Taiga Kodama, Kanagawa (JP); Tsutomu Igarashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 16/503,472

(22) Filed: Jul. 4, 2019

(65) Prior Publication Data

US 2019/0321817 A1    Oct. 24, 2019

Related U.S. Application Data

(63) Continuation of application No. PCT/JP2018/001043, filed on Jan. 16, 2018.

(30) Foreign Application Priority Data

Jan. 31, 2017 (JP) .................................. 2017-015930

(51) Int. Cl.
 *B01L 3/00* (2006.01)
 *B01D 46/00* (2006.01)
 (Continued)

(52) U.S. Cl.
 CPC .............. *B01L 3/502* (2013.01); *B01D 46/00* (2013.01); *C12M 27/02* (2013.01); *C12M 33/12* (2013.01);
 (Continued)

(58) Field of Classification Search
 CPC ............. B01L 3/502; B01L 2200/0605; B01L 2200/0647; B01L 2200/146;
 (Continued)

(56) References Cited

U.S. PATENT DOCUMENTS

2002/0043488 A1    4/2002  Letessier et al.
2006/0027264 A1 *  2/2006  Sann ....................... C12M 33/14
                                                                137/212
(Continued)

FOREIGN PATENT DOCUMENTS

JP    S62-78094 A       4/1987
JP    62121670 A   *    6/1987  ............. G03F 7/162
(Continued)

OTHER PUBLICATIONS

International Search Report issued in International Application No. PCT/JP2018/001043 dated Apr. 17, 2018.
(Continued)

*Primary Examiner* — Donnell A Long
(74) *Attorney, Agent, or Firm* — Solaris Intellectual Property Group, PLLC

(57) ABSTRACT

A dispensing device includes: a primary tank which accommodates a liquid; primary-side pressure adjusting means for adjusting pressure in an interior of the primary tank; a plurality of branch flow paths connected to the primary tank; and a plurality of secondary tanks which are provided corresponding to the plurality of branch flow paths, respectively, and each of which is connected to a corresponding branch flow path.

15 Claims, 20 Drawing Sheets

(51) Int. Cl.
*C12M 1/06* (2006.01)
*C12M 1/26* (2006.01)
*C12M 1/12* (2006.01)
*C12M 1/00* (2006.01)
*C12M 1/34* (2006.01)

(52) U.S. Cl.
CPC ............ *C12M 37/02* (2013.01); *C12M 39/00* (2013.01); *C12M 41/40* (2013.01); *B01L 2200/0605* (2013.01); *B01L 2200/0647* (2013.01); *B01L 2200/146* (2013.01); *B01L 2300/0681* (2013.01); *B01L 2300/0861* (2013.01); *B01L 2300/0877* (2013.01); *B01L 2300/14* (2013.01); *B01L 2400/0475* (2013.01); *B01L 2400/0487* (2013.01); *B01L 2400/0633* (2013.01)

(58) Field of Classification Search
CPC ..... B01L 2300/0681; B01L 2300/0861; B01L 2300/0877; B01L 2300/14; B01L 2400/0475; B01L 2400/0487; B01L 2400/0633; B01L 2400/0457; B01L 2300/0867; B01L 3/0293; B01D 46/00; C12M 27/02; C12M 33/12; C12M 37/02; C12M 39/00; C12M 41/40; C12M 29/00; B01J 2219/009; B01J 2219/00963; B01J 4/00
See application file for complete search history.

(56) References Cited

U.S. PATENT DOCUMENTS

| | | |
|---|---|---|
| 2010/0236340 A1 | 9/2010 | Lee et al. |
| 2013/0222488 A1 | 8/2013 | Miyashita et al. |
| 2014/0176647 A1 | 6/2014 | Miyashita et al. |

FOREIGN PATENT DOCUMENTS

| | | | |
|---|---|---|---|
| JP | S62-121670 A | | 6/1987 |
| JP | 2002-143751 A | | 5/2002 |
| JP | 2009-125027 A | | 6/2009 |
| JP | 2010-162446 A | | 7/2010 |
| JP | 2010162446 A | * | 7/2010 |
| JP | 2013-173240 A | | 9/2013 |
| WO | 2015/151339 A1 | | 10/2015 |

OTHER PUBLICATIONS

Written Opinion of the ISA issued in International Application No. PCT/JP2018/001043 dated Apr. 17, 2018.
Extended European Search Report dated Dec. 5, 2019, issued in corresponding EP Patent Application No. 18747465.5.
Office Action dated Sep. 29, 2020, issued by the EPO in corresponding EP Patent Application No. EP18747465.5.
English language translation of the following: Office action dated Aug. 19, 2020 from the KIPO in a Korean patent application No. 10-2019-7021040 corresponding to the instant patent application.

* cited by examiner

DISPENSING DEVICE AND LIQUID TRANSFER METHOD

CROSS-REFERENCE TO RELATED APPLICATIONS

This application is a continuation application of International Application No. PCT/JP2018/001043, filed Jan. 16, 2018, the disclosure of which is incorporated herein by reference in its entirety. Further, this application claims priority from Japanese Patent Application No. 2017-015930, filed Jan. 31, 2017, the disclosure of which is incorporated herein by reference in its entirety.

BACKGROUND

1. Technical Field

The disclosed technique relates to a dispensing device and a liquid transfer method.

2. Related Art

The following technique is known as a technique for transferring a liquid accommodated in a container to a plurality of different containers.

For example, JP2009-125027A discloses a technique for separating a culture solution from a tank containing the culture solution through a multi-way valve and simultaneously sending the culture solution to a plurality of culture vessels of a culture vessel set by using a pump. In this technique, n pieces of blocks each provided with m outlets having the same height with respect to a horizontal direction per one electromagnetic valve at an outlet of the multi-way valve are prepared. The solution is simultaneously put into the culture vessels located at the same height with respect to the horizontal direction in a block unit by on/off of the electromagnetic valve, and the same amount of culture solution is fed to culture media by controlling the electromagnetic valve in an outlet direction by a sensor on the outlet side.

Further, JP2009-125027A discloses a sampling method having a process of circulating a resist stripping solution in a compounding bath through a circulation compounding pipe, a process of disposing openable and closable extraction means in order at a plurality of places and disposing a sample bottle for each extraction means, a process of drawing the resist stripping solution circulating through the circulation compounding pipe into a sample pipe by a predetermined amount, and a process of extruding the resist stripping solution in the sample pipe into the sample bottle by using an inert gas.

SUMMARY

A dispensing device which automatically performs processing of extracting a predetermined amount of liquid from a container in which the liquid is accommodated and transferring the extracted liquid to each of a plurality of different containers is known. In this dispensing device, in many cases, a tube pump is used as a pump for performing liquid transfer. The tube pump is a pump which performs liquid transfer by a squeezing operation of the tube. In a case where a liquid to be treated contains fine particles vulnerable to a mechanical external force, such as gel beads, liposomes, cells, and cell clumps, there is a concern that the fine particles may be broken when the liquid passes through the tube pump. Therefore, in a case of handling the liquid containing fine particles vulnerable to a mechanical external force, it is not suitable to use a dispensing device in which liquid transfer by a tube pump is performed.

Therefore, a method of transferring a liquid to a plurality of subdivision containers by connecting a container that is a transfer source in which the liquid is accommodated to the plurality of subdivision containers that are transfer destinations by pipes, respectively, and pressurizing the interior of the container in which the liquid is accommodated is conceivable. In a case where the liquid containing fine particles vulnerable to a mechanical external force is transferred by using a method of performing liquid transfer by pressurization of the interior of the container that is the transfer source, it is desirable to perform the liquid transfer at a low pressure and a low speed. However, in the case of performing the liquid transfer at a low pressure and a low speed, the flow velocity of the liquid flowing through the pipe connected to each of the plurality of subdivision containers varies, and thus it becomes difficult to equalize the amount of the liquid which is transferred to the plurality of subdivision containers.

The disclosed technique is made in view of the above points and has an object to make it possible to transfer approximately the same amount of liquid to a plurality of transfer destinations while suppressing a mechanical external force which is applied to the liquid to be transferred.

A dispensing device according to the disclosed technique comprises: a primary tank which accommodates a liquid; primary-side pressure adjusting means for adjusting pressure in an interior of the primary tank; a plurality of branch flow paths connected to the primary tank; and a plurality of secondary tanks which are provided corresponding to the plurality of branch flow paths, respectively, and each of which is connected to a corresponding branch flow path.

In the dispensing device according to the disclosed technique, in a state where a gas in an interior of each of the plurality of secondary tanks is retained in the interior of the secondary tank, the primary-side pressure adjusting means may pressurize an interior of the primary tank to transfer the liquid from the primary tank to each of the plurality of secondary tanks.

The dispensing device according to the disclosed technique may further comprise secondary-side pressure adjusting means for adjusting pressure in the interior of each of the plurality of secondary tanks. The secondary-side pressure adjusting means may open the interior of each of the plurality of secondary tanks to the atmosphere before the liquid transferred into the interior of each of the plurality of secondary tanks is discharged.

The dispensing device according to the disclosed technique may further comprise: a plurality of first valves each provided in the middle of each of the plurality of branch flow paths; a plurality of discharge flow paths which are respectively connected to the plurality of secondary tanks, and through each of which the liquid which is discharged from each of the plurality of secondary tanks flows; a plurality of second valves each provided in the middle of each of the plurality of discharge flow paths; and a control part which controls each of the plurality of first valves to be in an open state and controls each of the plurality of second valves to be in a closed state, in a case of transferring the liquid from the primary tank to each of the plurality of secondary tanks, and controls each of the plurality of first valves to be in a closed state and controls each of the plurality of second valves to be in an open state, in a case of discharging the liquid accommodated in the interior of each of the plurality of secondary tanks from each of the plurality of secondary tanks.

The dispensing device according to the disclosed technique may further comprise: a state detection part which detects a state of an interior of at least one of the plurality of secondary tanks; a plurality of valves each provided in the middle of each of the plurality of branch flow paths; and a control part which controls opening and closing of each of the plurality of valves, based on a detection result of the state detection part.

The state detection part may include a pressure sensor which is provided in at least one of the plurality of secondary tanks and detects the pressure in the interior of the secondary tank.

The state detection part may include a plurality of pressure sensors which are provided corresponding to the plurality of secondary tanks, respectively, and each of which detects pressure in an interior of a corresponding secondary tank. The control part may control the valve corresponding to the secondary tank determined that the amount of accommodated liquid which is estimated from the pressure detected by the pressure sensor has reached a predetermined amount, among the plurality of secondary tanks, to be in a closed state, in a case where the liquid is transferred from the primary tank to each of the plurality of secondary tanks.

The dispensing device according to the disclosed technique may further comprise: secondary-side pressure adjusting means for adjusting the pressure in the interior of each of the plurality of secondary tanks, based on the pressure detected by each of the plurality of pressure sensors, in a case where the liquid is transferred from the primary tank to each of the plurality of secondary tanks. The secondary-side pressure adjusting means may decompress the interior of the secondary tank determined that the amount of accommodated liquid which is estimated from the pressure detected by the pressure sensor is smaller than a predetermined amount, among the plurality of secondary tanks, and pressurize the interior of the secondary tank determined that the amount of accommodated liquid which is estimated from the pressure detected by the pressure sensor is larger than the predetermined amount, among the plurality of secondary tanks, in a case where the liquid is transferred from the primary tank to each of the plurality of secondary tanks.

The state detection part may include a level sensor which is provided in at least one of the plurality of secondary tanks and detects a height of a liquid level of the liquid accommodated in the interior of the secondary tank.

The state detection part may include a plurality of level sensors which are provided corresponding to the plurality of secondary tanks, respectively, and each of which detects a height of a liquid level of a liquid accommodated in an interior of a corresponding secondary tank. The control part may control the valve corresponding to the secondary tank determined that the amount of accommodated liquid which is estimated from the height of the liquid level detected by the level sensor has reached a predetermined amount, among the plurality of secondary tanks, to be in a closed state, in a case where the liquid is transferred from the primary tank to each of the plurality of secondary tanks.

The dispensing device according to the disclosed technique may further comprise secondary-side pressure adjusting means for adjusting the pressure in the interior of each of the plurality of secondary tanks, based on the height of the liquid level detected by each of the plurality of level sensors, in a case where the liquid is transferred from the primary tank to each of the plurality of secondary tanks. The secondary-side pressure adjusting means may decompress the interior of the secondary tank determined that the amount of accommodated liquid which is estimated from the height of the liquid level detected by the level sensor is smaller than a predetermined amount, among the plurality of secondary tanks, and pressurize the interior of the secondary tank determined that the amount of accommodated liquid which is estimated from the height of the liquid level detected by the level sensor is larger than the predetermined amount, among the plurality of secondary tanks, in a case where the liquid is transferred from the primary tank to each of the plurality of secondary tanks.

The primary tank may have a plurality of outflow ports connected to the plurality of branch flow paths, respectively.

The dispensing device according to the disclosed technique may further comprise: a first filter which suppresses inflow of unnecessary components contained in a gas which is supplied to the primary tank into the interior of the primary tank in a case where the primary-side pressure adjusting means pressurizes the interior of the primary tank; and a second filter which suppresses inflow of unnecessary components contained in a gas which is supplied to the secondary tank into the interior of the secondary tank in a case where the secondary-side pressure adjusting means pressurizes the interior of the secondary tank.

Each of the plurality of secondary tanks may include a first portion which accommodates the liquid which is transferred from the primary tank, and a second portion which is connected to the first portion through a connection pipe and has a flow port into which a gas which is supplied to the secondary tank flows in a case where the secondary-side pressure adjusting means pressurizes the interior of the secondary tank, and the second filter may be provided in the middle of the connection pipe.

It is preferable that volumes of the plurality of branch flow paths are equal to each other.

The primary tank may have a stirring function of stirring the liquid accommodated in the interior of the primary tank.

A liquid transfer method according to the disclosed technique is a liquid transfer method for transferring the liquid by using the dispensing device, the method comprising: accommodating the liquid in the primary tank; and transferring the liquid from the primary tank to each of the plurality of secondary tanks by pressurizing the interior of the primary tank in a state where a gas in the interior of each of the plurality of secondary tanks is retained in the interior of the secondary tank.

According to the disclosed techniques, it becomes possible to transfer approximately the same amount of liquids to a plurality of transfer destinations while suppressing a mechanical external force which is applied to the liquid to be transferred.

BRIEF DESCRIPTION OF THE DRAWINGS

Exemplary embodiments according to the technique of the present disclosure will be described in detail based on the following figures, wherein.

DETAILED DESCRIPTION

Figure 1:
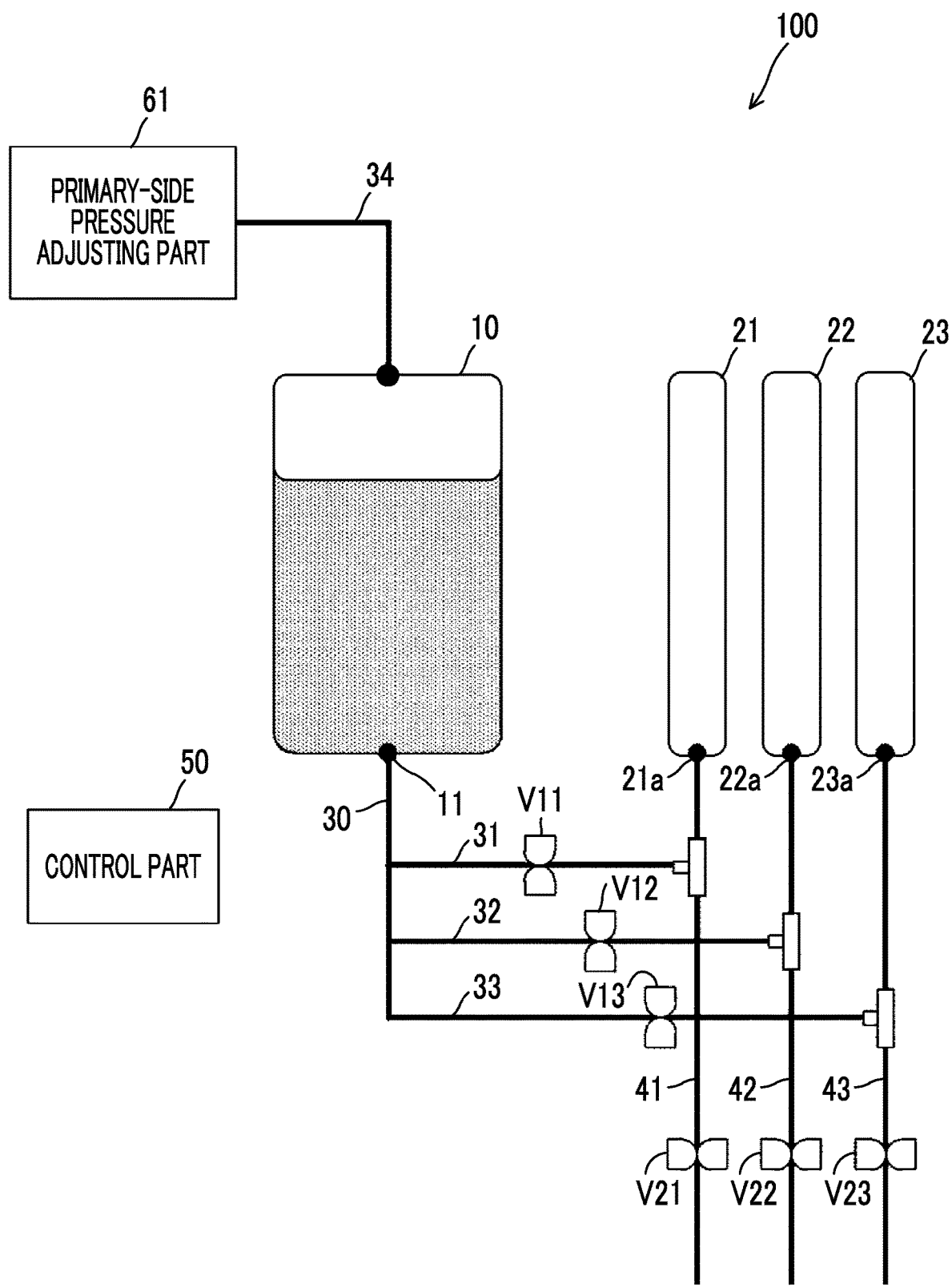
FIG. 1 is a diagram showing a configuration of a dispensing device according to an embodiment of the disclosed technique.

Hereinafter, an example of an embodiment of the disclosed technique will be described with reference to the drawings. In each drawing, identical or equivalent constituent elements and portions are denoted by the same reference numerals.

First Embodiment

FIG. 1 is a diagram showing the configuration of a dispensing device 100 according to a first embodiment of the disclosed technique. The dispensing device 100 is configured to include a primary tank 10, a plurality of secondary tanks 21, 22, and 23, a control part 50, and a primary-side pressure adjusting part 61. In this embodiment, a case where the dispensing device 100 comprises three secondary tanks 21, 22, and 23 is illustrated. However, the number of secondary tanks which the dispensing device 100 comprises may be two or four or more.

The primary tank 10 is a container for accommodating a liquid to be transferred. An outflow port 11 is provided in a bottom portion of the primary tank 10, and the liquid flowing out to the outside of the primary tank 10 passes through the outflow port 11. A primary-side discharge flow path 30 is connected to the outflow port 11, and branch flow paths 31, 32, and 33 are connected to the primary-side discharge flow path 30.

The secondary tank 21 is connected to the branch flow path 31 and a secondary-side discharge flow path 41. A flow port 21a is provided in a bottom portion of the secondary tank 21, and the liquid flowing from the outside of the secondary tank 21 into the interior of the secondary tank 21 and the liquid flowing out from the interior of the secondary tank 21 to the outside of the secondary tank 21 pass through the flow port 21a.

The secondary tank 22 is connected to the branch flow path 32 and a secondary-side discharge flow path 42. A flow port 22a is provided in a bottom portion of the secondary tank 22, and the liquid flowing from the outside of the secondary tank 22 into the interior of the secondary tank 22 and the liquid flowing out from the interior of the secondary tank 22 to the outside of the secondary tank 22 pass through the flow port 22a.

The secondary tank 23 is connected to the branch flow path 33 and a secondary-side discharge flow path 43. A flow port 23a is provided in a bottom portion of the secondary tank 23, and the liquid flowing from the outside of the secondary tank 23 into the interior of the secondary tank 23 and the liquid flowing out from the interior of the secondary tank 23 to the outside of the secondary tank 23 pass through the flow port 23a.

Each of the secondary tanks 21, 22, and 23 is made of a material, such as glass, plastic, or metal, in which volume does not change due to pressurization of the interior. Further, the secondary tanks 21, 22, and 23 have the same shape and volume as each other. The expression, the same shape and volume as each other, means that the shape and volume are the same within an allowable error range.

Inflow-side valves V11, V12, and V13 are provided in the middle of the branch flow paths 31, 32, and 33, respectively. Discharge-side valves V21, V22, and V23 are provided in the middle of the secondary-side discharge flow paths 41, 42, and 43, respectively. Each of the inflow-side valves V11, V12, and V13 and the discharge-side valves V21, V22, and V23 has the form of an electromagnetic valve which is opened and closed according to a control signal which is supplied from the control part 50.

The primary-side pressure adjusting part 61 is connected to the primary tank 10 through a pipe 34. The primary-side pressure adjusting part 61 is configured to include a pressure applying device such as a compressor or a syringe pump, for example, and changes the pressure in the interior of the primary tank 10 under the control of the control part 50.

The control part 50 controls the transfer of the liquid from the primary tank 10 to each of the secondary tanks 21, 22, and 23 and the discharge of the liquid from the interior of each of the secondary tanks 21, 22, and 23 to the outside of each of the secondary tanks 21, 22, and 23. Specifically, the control part 50 controls the opening and closing of the inflow-side valves V11, V12, and V13 and the discharge-side valves V21, V22, and V23. Further, the control part 50 controls the driving of the primary-side pressure adjusting part 61, thereby adjusting the pressure in the interior of the primary tank 10. The control part 50 is connected to each of the primary-side pressure adjusting part 61, the inflow-side valves V11, V12, and V13, and the discharge-side valves V21, V22, and V23 through individual control wires. However, from the viewpoint of avoiding complication of the drawing, illustration of these control wires is omitted. The same applies to the other drawings which are referred to below. The control part 50 controls each of the primary-side pressure adjusting part 61, the inflow-side valves V11, V12, and V13, and the discharge-side valves V21, V22, and V23 by supplying a control signal through the control wire.

The dispensing device 100 performs dispensing processing of transferring the liquid accommodated in the interior of the primary tank 10 to each of the secondary tanks 21, 22, and 23 and then discharging the liquid from each of the secondary tanks 21, 22, and 23 to the outside of each of the secondary tanks 21, 22, and 23. An operation in a case where the dispensing device 100 performs the dispensing processing will be described in detail below.

Figure 2:
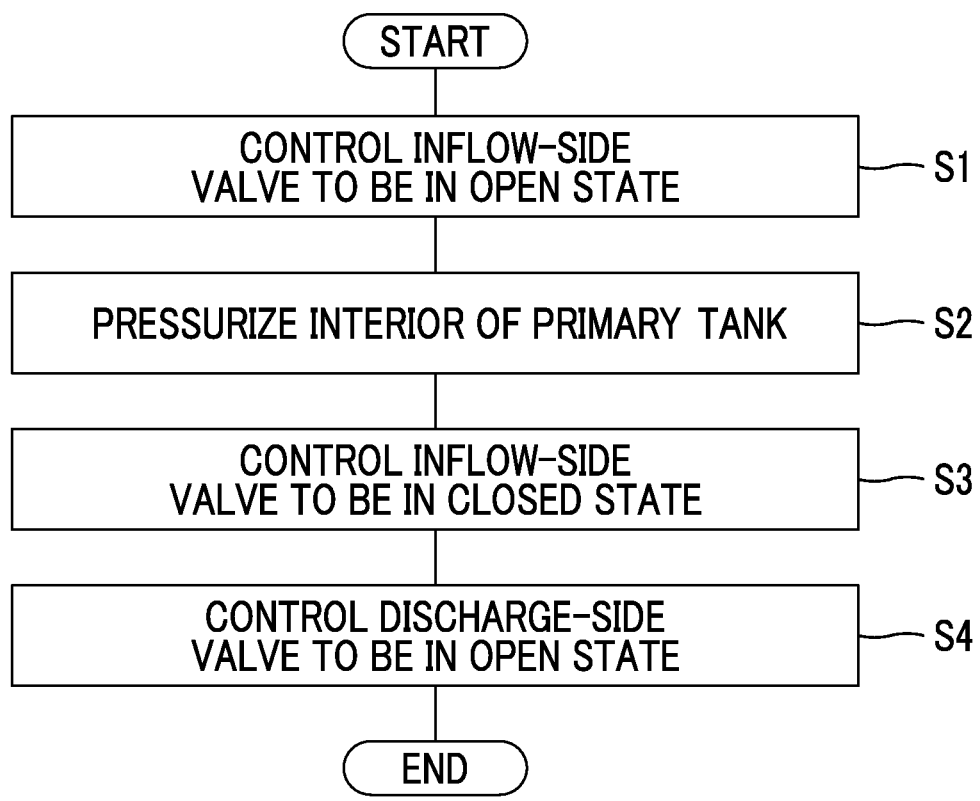
FIG. 2 is a flowchart showing a flow of processing which is carried out by a control part in a case where the dispensing device according to the embodiment of the disclosed technique performs dispensing processing.

FIG. 2 is a flowchart showing a flow of processing which is carried out by the control part 50 in a case where the dispensing device 100 performs the dispensing processing. In the initial state, it is assumed that the liquid is accommodated in the interior of the primary tank 10 and the inflow-side valves V11, V12, and V13 and the discharge-side valves V21, V22, and V23 are in a closed state.

In step S1, the control part 50 controls the inflow-side valves V11, V12, and V13 to be in an open state.

Figure 3:
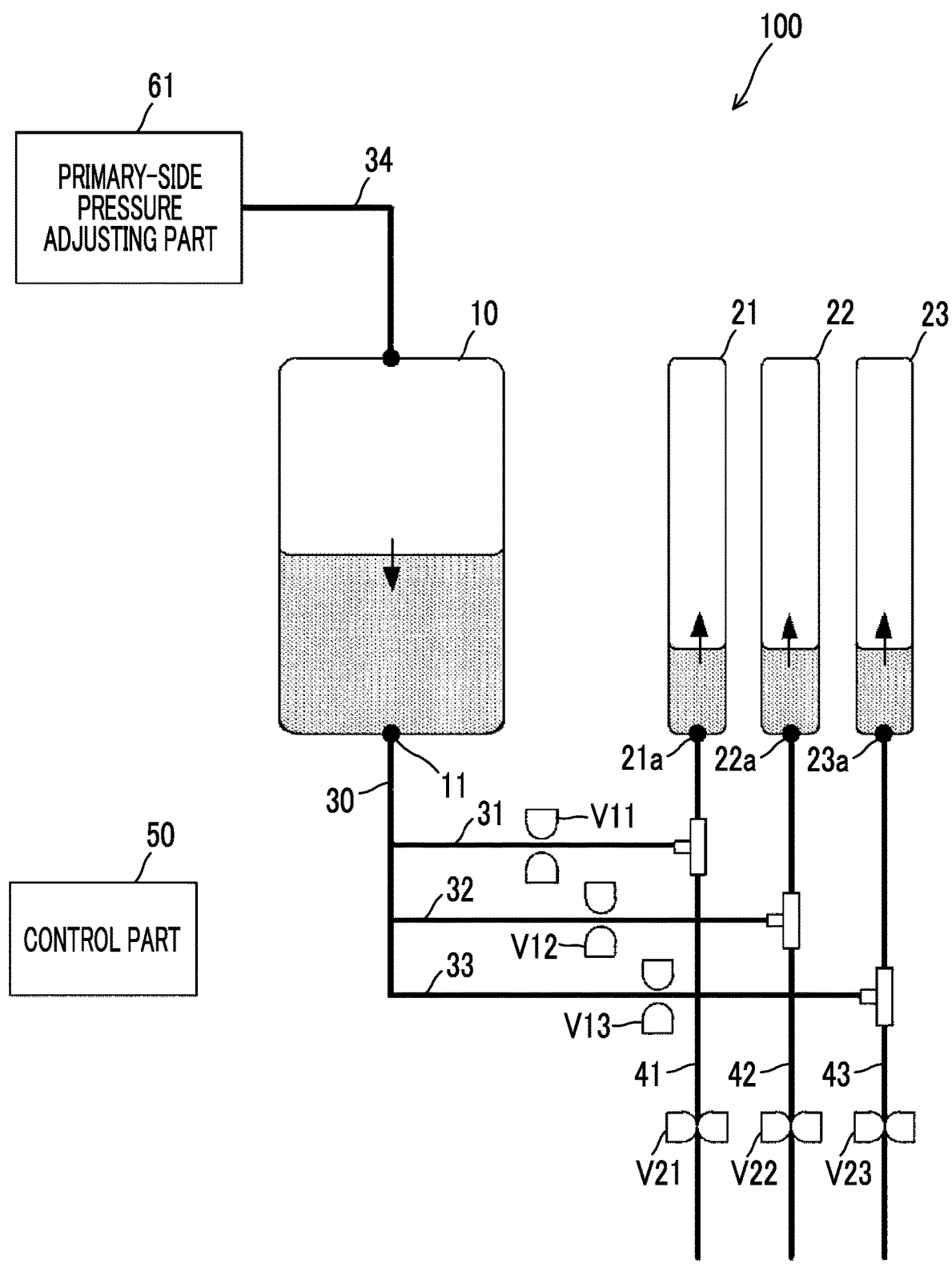
FIG. 3 is a diagram showing the state of the dispensing device in a stage of pressurizing the interior of a primary tank.

In step S2, the control part 50 pressurizes the interior of the primary tank 10 by controlling the primary-side pressure adjusting part 61. FIG. 3 is a diagram showing the state of the dispensing device 100 in a stage where the processing of step S2 is being carried out. The liquid accommodated in the interior of the primary tank 10 is transferred to each of the secondary tanks 21, 22, and 23 through the branch flow paths 31, 32, and 33 by pressurizing the interior of the primary tank 10 while making the inflow-side valves V11, V12, and V13 be in an open state. The liquid is injected from the flow ports 21a, 22a, and 23a provided in the bottom portions of the respective secondary tanks 21, 22, and 23 into the respective secondary tanks 21, 22, and 23.

The transfer of the liquid from the primary tank 10 to each of the secondary tanks 21, 22, and 23 is performed in a state where a gas in the interior of each of the secondary tanks 21, 22, and 23 is retained in the interior of the secondary tank. Therefore, the pressure in the interior of each of the secondary tanks 21, 22, and 23 increases according to an increase in the amount of the liquid which is injected into each of the secondary tanks 21, 22, and 23. Here, the volume and pressure of the gas in the interior of each of the secondary tanks 21, 22, and 23 in the initial state before the liquid is injected into each of the secondary tanks 21, 22, and 23 are set to be V0 and P0, respectively. The volume and pressure of the gas in the interior of each of the secondary tanks 21, 22, and 23 in a state where the liquid has been injected into the interior of each of the secondary tanks 21, 22, and 23 are set to be V1 and P1, respectively. In this case, the following expression (1) is established with respect to the volumes V0 and V1 and the pressures P0 and P1.

$$P0 \times V0 = P1 \times V1 \quad (1)$$

That is, in a case where the liquid is transferred to each of the secondary tanks 21, 22, and 23 in a state where each of the secondary tanks 21, 22, and 23 is hermetically sealed, the product of the volume and the pressure of the gas in the interior of each of the secondary tanks 21, 22, and 23 is always constant.

In a case where the pressure in the interior of each of the secondary tanks 21, 22, and 23 becomes equal to the pressure in the interior of the primary tank 10, an equilibrium state is created where the flow of the liquid from the primary tank 10 to each of the secondary tanks 21, 22, and 23 is stopped. In this way, the liquid transfer from the primary tank 10 to each of the secondary tanks 21, 22, and 23 is completed.

Figure 4:
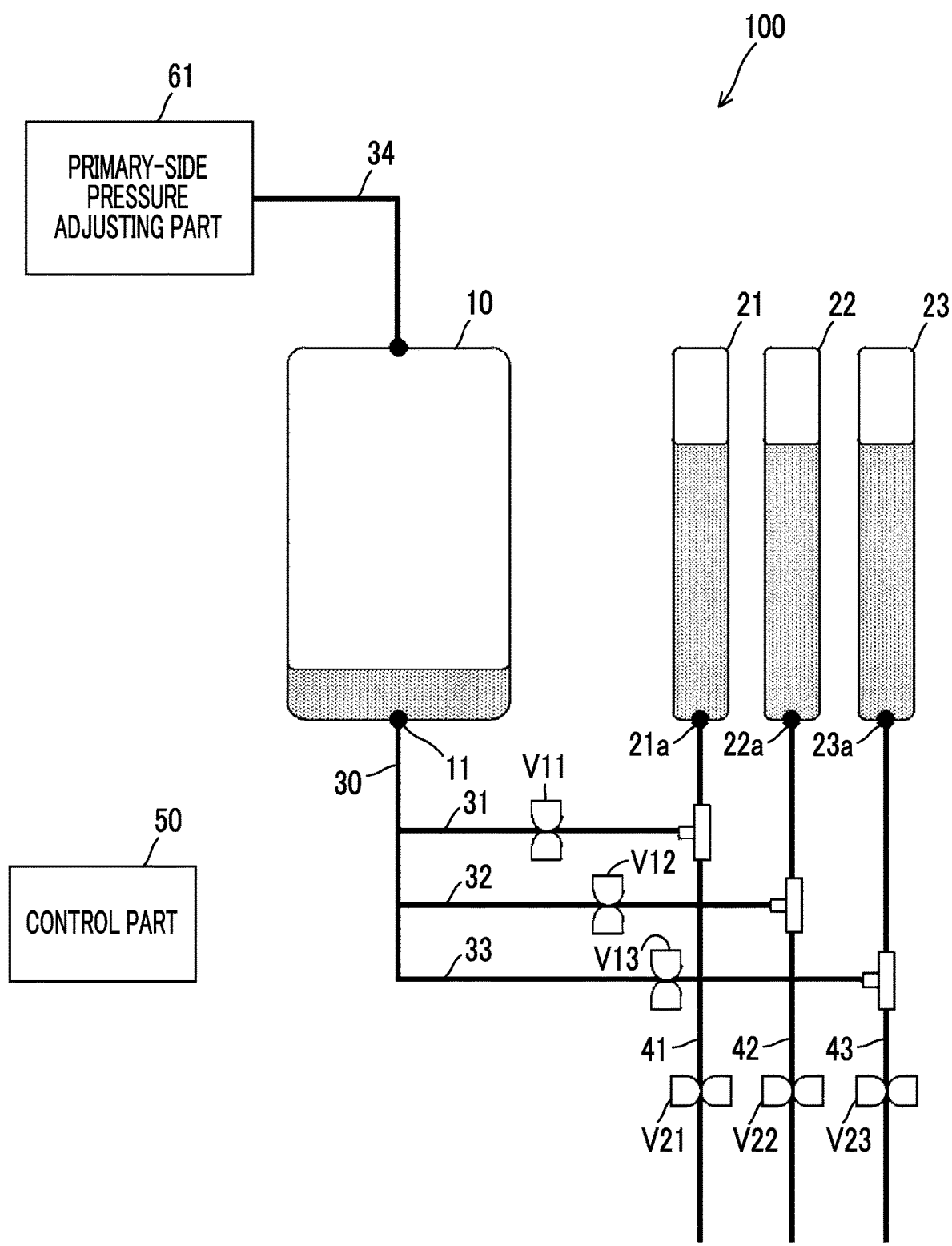
FIG. 4 is a diagram showing the state of the dispensing device in a stage where an inflow-side valve is controlled to be in a closed state.

In a case where the liquid transfer from the primary tank 10 to each of the secondary tanks 21, 22, and 23 is completed, in step S3, the control part 50 controls the inflow-side valves V11, V12, and V13 to be in a closed state. FIG. 4 is a diagram showing the state of the dispensing device 100 in a stage where the processing of step S3 has been carried out. Approximately the same amount of liquid is accommodated in each of the secondary tanks 21, 22, and 23. Thereafter, the control part 50 stops the pressurization of the interior of the primary tank 10 by the primary-side pressure adjusting part 61.

Figure 5:
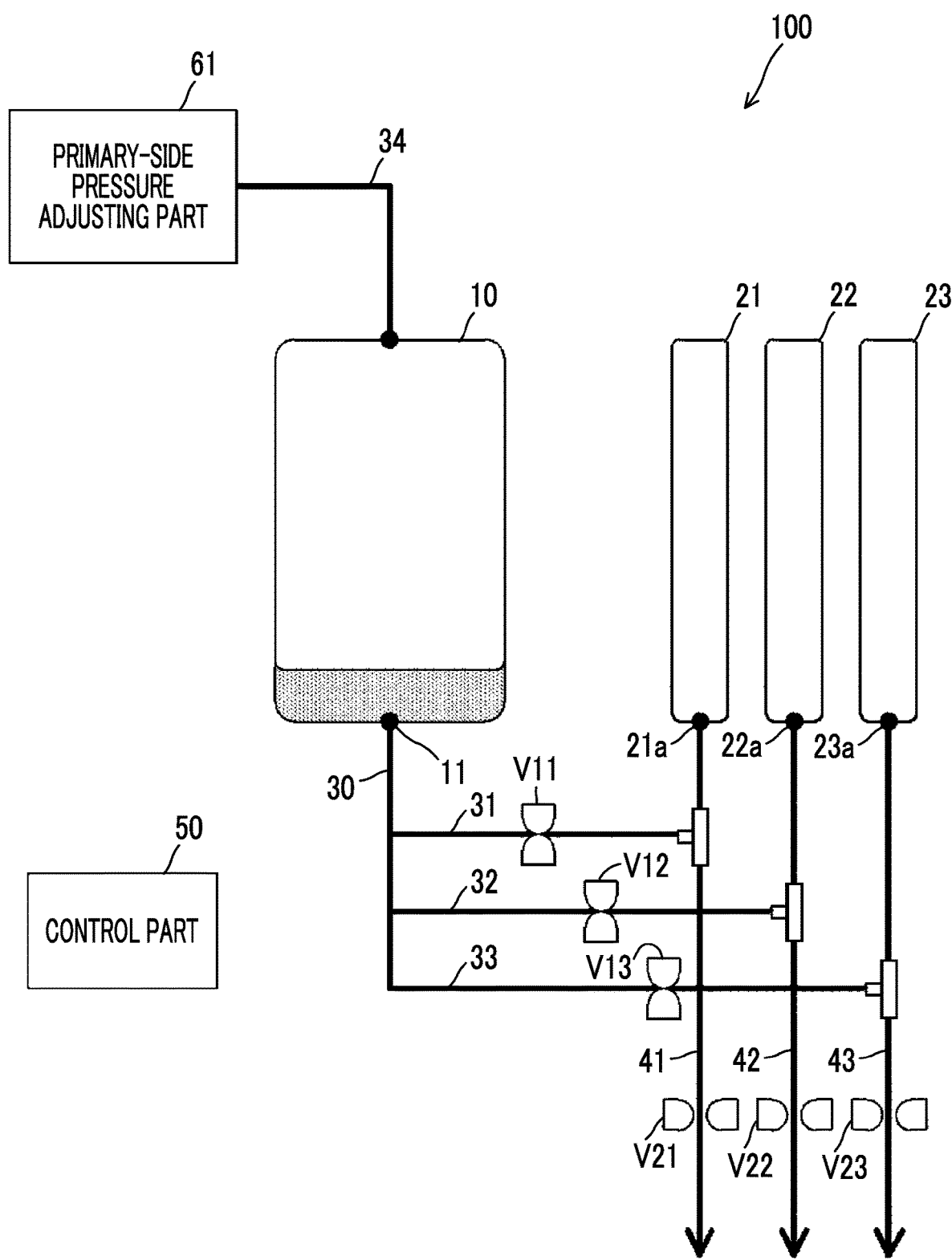
FIG. 5 is a diagram showing the state of the dispensing device in a stage where a discharge-side valve is controlled to be in an open state.

In step S4, the control part 50 controls the discharge-side valves V21, V22, and V23 to be in an open state. FIG. 5 is a diagram showing the state of the dispensing device 100 in a stage where the processing of step S4 has been carried out. In a case where the discharge-side valves V21, V22, and V23 are controlled to be in the open state, the liquid accommodated in each of the secondary tanks 21, 22, and 23 is discharged to the outside of the secondary tanks 21, 22, and 23 and is transferred to the next transfer destination through the secondary-side discharge flow paths 41, 42, and 43. The discharge of the liquid to the outside of the secondary tanks 21, 22, and 23 is performed by the residual pressure in the interior of each of the secondary tanks 21, 22, and 23 and the gravity. The control part 50 may simultaneously perform the discharge of the liquid from the respective secondary tanks 21, 22, and 23 by simultaneously controlling the discharge-side valves V21, V22, and V23 to be in an open state. Further, the control part 50 may perform the discharge of the liquid from the respective secondary tanks 21, 22, and 23 in stages by controlling the discharge-side valves V21, V22, and V23 to be in an open state in order.

For example, a subdivision container (not shown) which is a final transfer destination of the liquid is disposed at a terminal end portion of each of the secondary-side discharge flow paths 41, 42, and 43, and the liquid is injected into each of the subdivision containers. The transfer destination of the liquid which is discharged from each of the secondary tanks 21, 22, and 23 may be, for example, a processing device which carries out predetermined processing on the liquid.

As described above, according to the dispensing device 100 of this embodiment, the transfer of the liquid from the primary tank 10 to each of the secondary tanks 21, 22, and 23 is performed by pressurization of the interior of the primary tank 10. Further, the discharge of the liquid to the outside of the secondary tanks 21, 22, and 23 is performed by the residual pressure in the interior of each of the secondary tanks 21, 22, and 23 and the gravity. In this way, it is possible to reduce a mechanical external force which is applied to the liquid during the liquid transfer, as compared with a case where liquid transfer is performed using a tube pump. Therefore, the dispensing device 100 according to this embodiment can be suitably used in a case of handling a liquid containing fine particles vulnerable to a mechanical external force, such as gel beads, liposomes, cells, and cell clumps.

Further, according to the dispensing device 100 of this embodiment, the liquid is transferred from the primary tank 10 to each of the secondary tanks 21, 22, and 23 in a state where the gas in the interior of each of the secondary tanks 21, 22, and 23 is retained in the interior of the secondary tank. In this way, it becomes possible to autonomously perform the processing of distributing approximately the same amount of liquid from the primary tank 10 to each of the secondary tanks 21, 22, and 23.

That is, in a case where the liquid is transferred to each of the secondary tanks 21, 22, and 23 in a state where each of the secondary tanks 21, 22, and 23 is hermetically sealed, as shown in the expression (1) describe above, the product of the volume and the pressure of the gas in the interior of each of the secondary tanks 21, 22, and 23 becomes always constant. Therefore, the pressure in the interior of each of the secondary tanks 21, 22, and 23 increases according to an increase in the amount of the liquid which is injected into each of the secondary tanks 21, 22, and 23. Here, a case where the amount of the liquid injected into, for example, the secondary tank 21 becomes larger than those in the other secondary tanks 22 and 23 during a stage where the liquid transfer to each of the secondary tanks 21, 22, and 23 is being performed is supposed. In this case, the pressure in the interior of the secondary tank 21 becomes higher than the pressure in the interior of each of the other secondary tanks 22 and 23. In this way, the inflow of the liquid into the secondary tank 21 acts to be suppressed as compared with the other secondary tanks 22 and 23. That is, while the liquid transfer to each of the secondary tanks 21, 22, and 23 is being performed, the amount of the liquid which is injected into each of the secondary tanks 21, 22, and 23 is adjusted such that a pressure difference between the interiors of the secondary tanks 21, 22, and 23 is reduced. As a result, the liquid is substantially equally distributed from the primary tank 10 to each of the secondary tanks 21, 22, and 23.

As is apparent from the above description, according to the dispensing device 100 of this embodiment, it becomes possible to transfer approximately the same amount of liquid to a plurality of transfer destinations while suppressing a mechanical external force which is applied to the liquid to be transferred. According to the dispensing device 100 of this embodiment, for example, the dispensing device 100 can be suitably used for a use or the like of distributing a liquid, in which microcapsules in which a functional liquid exhibiting a desired function is encapsulated are dispersed, to a plurality of subdivision containers.

In a case where a gas staying in the interior of each of the branch flow paths 31, 32, and 33 flows into the interior of each of the secondary tanks 21, 22, and 23 in a process of transferring the liquid from the primary tank 10 to the secondary tanks 21, 22, and 23, the pressure in the interior of each of the secondary tanks 21, 22, and 23 increases. That is, it is assumed that the gas staying in the interior of each of the branch flow paths 31, 32, and 33 affects the pressure in the interior of each of the secondary tanks 21, 22, and 23. Therefore, it is preferable to minimize the difference in the influence of the gas staying in the interior of each of the branch flow paths 31, 32, and 33 on the pressure in the interior of each of the secondary tanks 21, 22, and 23 by making the volumes of the branch flow paths 31, 32, and 33 equal to each other. The expression, the volumes being the same as each other, means that the volumes are the same within an allowable error range.

Second Embodiment

Figure 6:
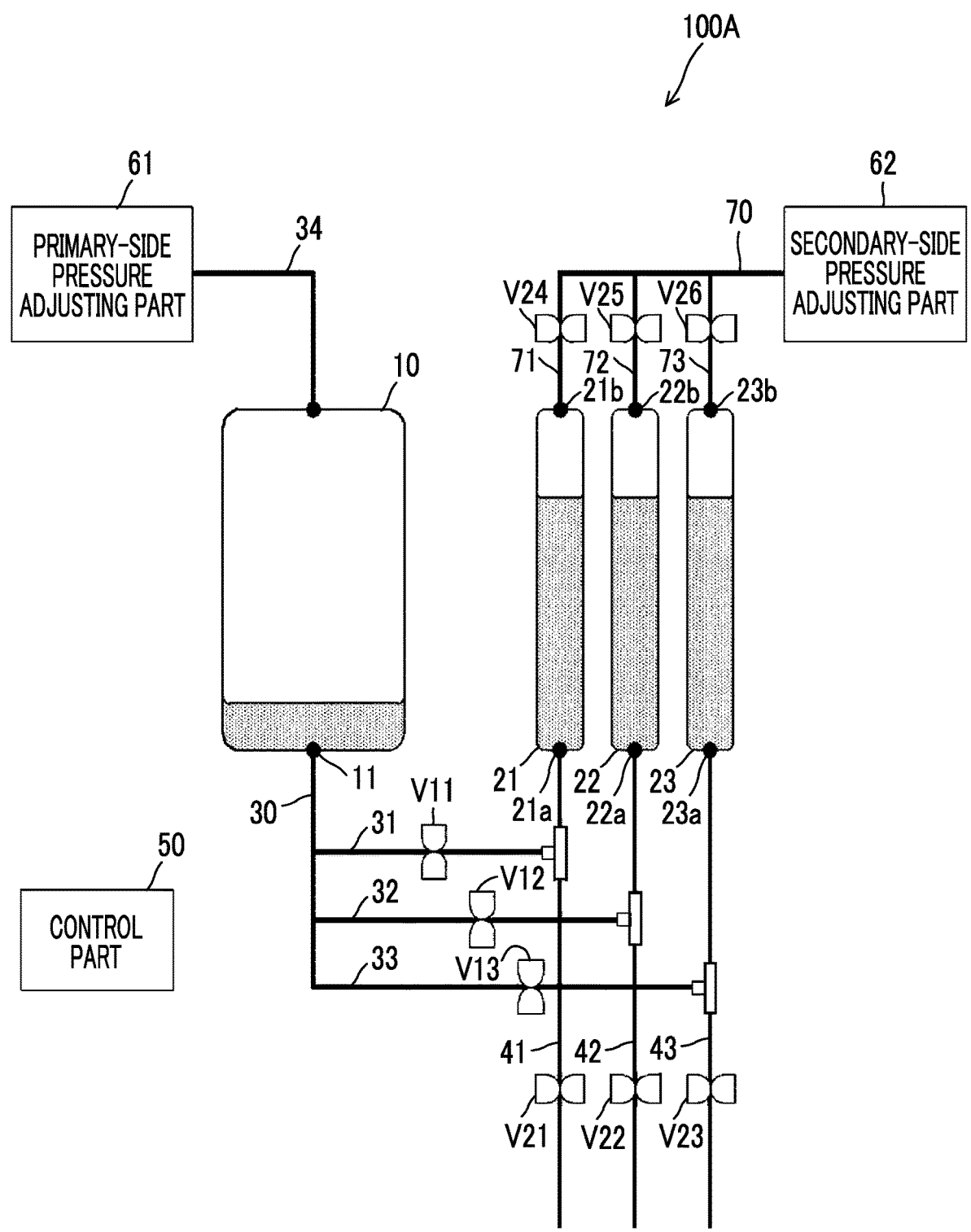
FIG. 6 is a diagram showing a configuration of a dispensing device according to another embodiment of the disclosed technique.

FIG. 6 is a diagram showing the configuration of a dispensing device 100A according to a second embodiment of the disclosed technique. The dispensing device 100A according to the second embodiment is different from the dispensing device 100 according to the first embodiment in that the dispensing device 100A further includes a secondary-side pressure adjusting part 62 and pressure adjusting valves V24, V25, and V26.

The secondary-side pressure adjusting part 62 is connected to each of the secondary tanks 21, 22, and 23 through a common pipe 70 and individual pipes 71, 72, and 73. The secondary-side pressure adjusting part 62 is configured to include a pressure applying device such as a compressor or a syringe pump, for example, and has a function of pressurizing and decompressing the interior of each of the secondary tanks 21, 22, and 23. Further, the secondary-side pressure adjusting part 62 has a function of opening the interior of each of the secondary tanks 21, 22, and 23 to the atmosphere.

Gas flow ports 21b, 22b, and 23b are provided in upper portions of the secondary tanks 21, 22, and 23, respectively, and the gas flow ports 21b, 22b, and 23b are respectively connected to the individual pipes 71, 72, and 73.

Pressure adjusting valves V24, V25, and V26 are provided in the middle of the individual pipes 71, 72, and 73, respectively. Each of the pressure adjusting valves V24, V25, and V26 has the form of an electromagnetic valve which is opened and closed according to a control signal which is supplied from the control part 50.

In the dispensing device 100A according to the second embodiment, the control part 50 also performs opening/closing control of the pressure adjusting valves V24, V25, and V26, in addition to the opening/closing control of the inflow-side valves V11, V12, and V13 and the discharge-side valves V21, V22, and V23. Further, the dispensing device 100A also performs adjustment of the pressure in the interior of each of the secondary tanks 21, 22, and 23 by controlling the operation of the secondary-side pressure adjusting part 62, in addition to the adjustment of the pressure in the interior of the primary tank 10.

Figure 7:
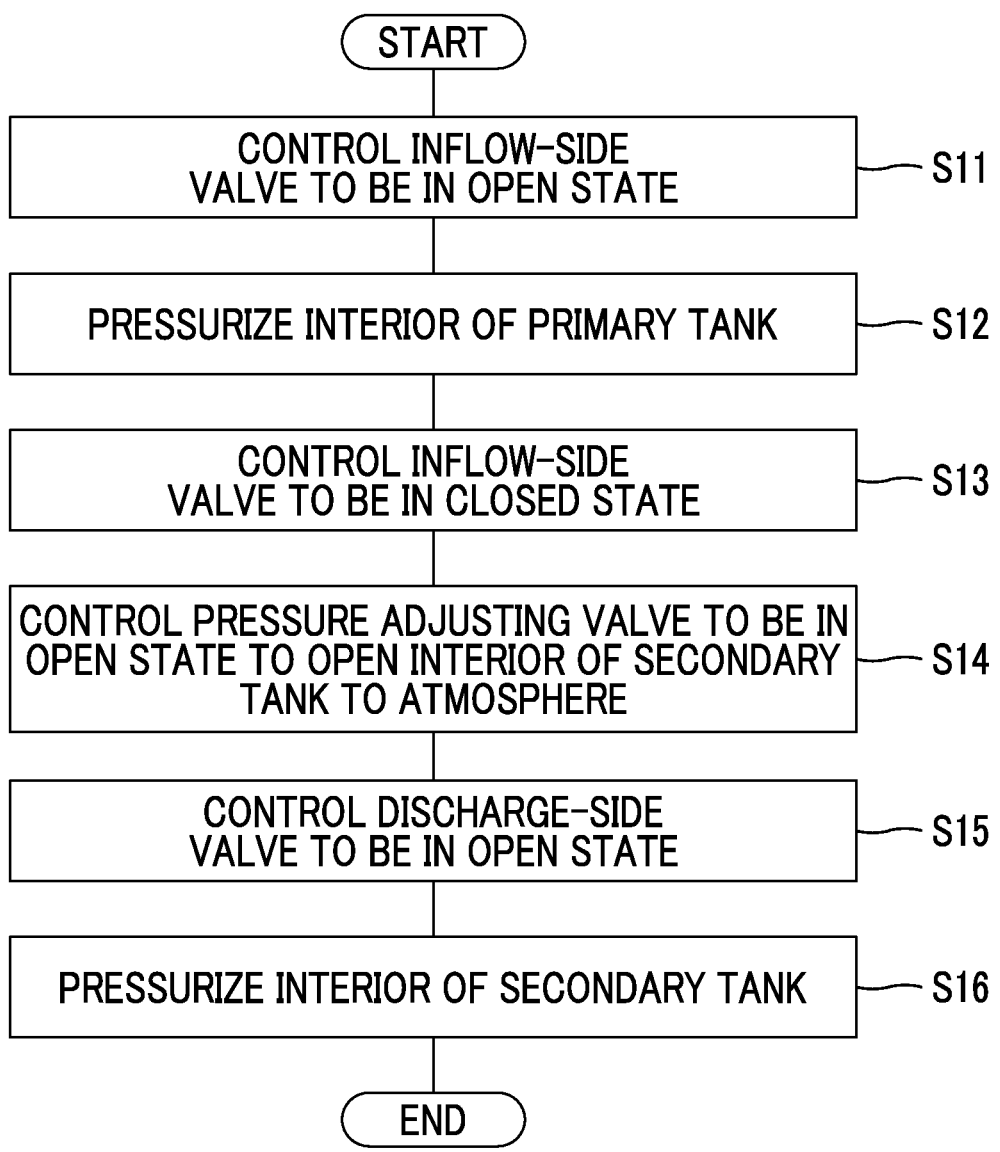
FIG. 7 is a flowchart showing a flow of processing which is carried out by the control part in a case where the dispensing device according to another embodiment of the disclosed technique performs dispensing processing.

FIG. 7 is a flowchart showing a flow of processing which is carried out by the control part 50 in a case where the dispensing device 100A performs the dispensing processing. In the initial state, it is assumed that the liquid is accommodated in the interior of the primary tank 10 and the inflow-side valves V11, V12, and V13, the discharge-side valves V21, V22, and V23, and the pressure adjusting valves V24, V25, and V26 are in a closed state.

In step S11, the control part 50 controls the inflow-side valves V11, V12, and V13 to be in an open state.

In step S12, the control part 50 pressurizes the interior of the primary tank 10 by controlling the primary-side pressure adjusting part 61. The liquid accommodated in the interior of the primary tank 10 is transferred to each of the secondary tanks 21, 22, and 23 through the branch flow paths 31, 32, and 33 by pressurizing the interior of the primary tank 10 while making the inflow-side valves V11, V12, and V13 be in an open state. The liquid is injected from the flow ports 21a, 22a, and 23a provided in the bottom portions of the respective secondary tanks 21, 22, and 23 into the respective secondary tanks 21, 22, and 23.

While the liquid transfer from the primary tank 10 to each of the secondary tanks 21, 22, and 23 is being performed, the pressure adjusting valves V24, V25, and V26 are maintained in a closed state. That is, the transfer of the liquid from the primary tank 10 to each of the secondary tanks 21, 22, and 23 is performed in a state where the gas in the interior of each of the secondary tanks 21, 22, and 23 is retained in the interior of the secondary tank. Therefore, the pressure in the interior of each of the secondary tanks 21, 22, and 23 increases according to an increase in the amount of the liquid which is injected into each of the secondary tanks 21, 22, and 23. In a case where the pressure in the interior of each of the secondary tanks 21, 22, and 23 becomes equal to the pressure in the interior of the primary tank 10, an equilibrium state is created in which the flow of the liquid from the primary tank 10 to each of the secondary tanks 21, 22, and 23 is stopped. Due to the liquid transfer to each of the secondary tanks 21, 22, and 23, the pressure in the interior of each of the secondary tanks 21, 22, and 23 increases to a pressure higher than the atmospheric pressure.

In a case where the liquid transfer from the primary tank 10 to each of the secondary tanks 21, 22, and 23 is completed, in step S13, the control part 50 controls the inflow-side valves V11, V12, and V13 to be in a closed state. FIG. 6 shows the state of the dispensing device 100A in a stage where the processing of step S13 has been carried out. Approximately the same amount of liquid is accommodated in each of the secondary tanks 21, 22, and 23. Thereafter, the control part 50 stops the pressurization of the interior of the primary tank 10 by the primary-side pressure adjusting part 61.

Figure 8:
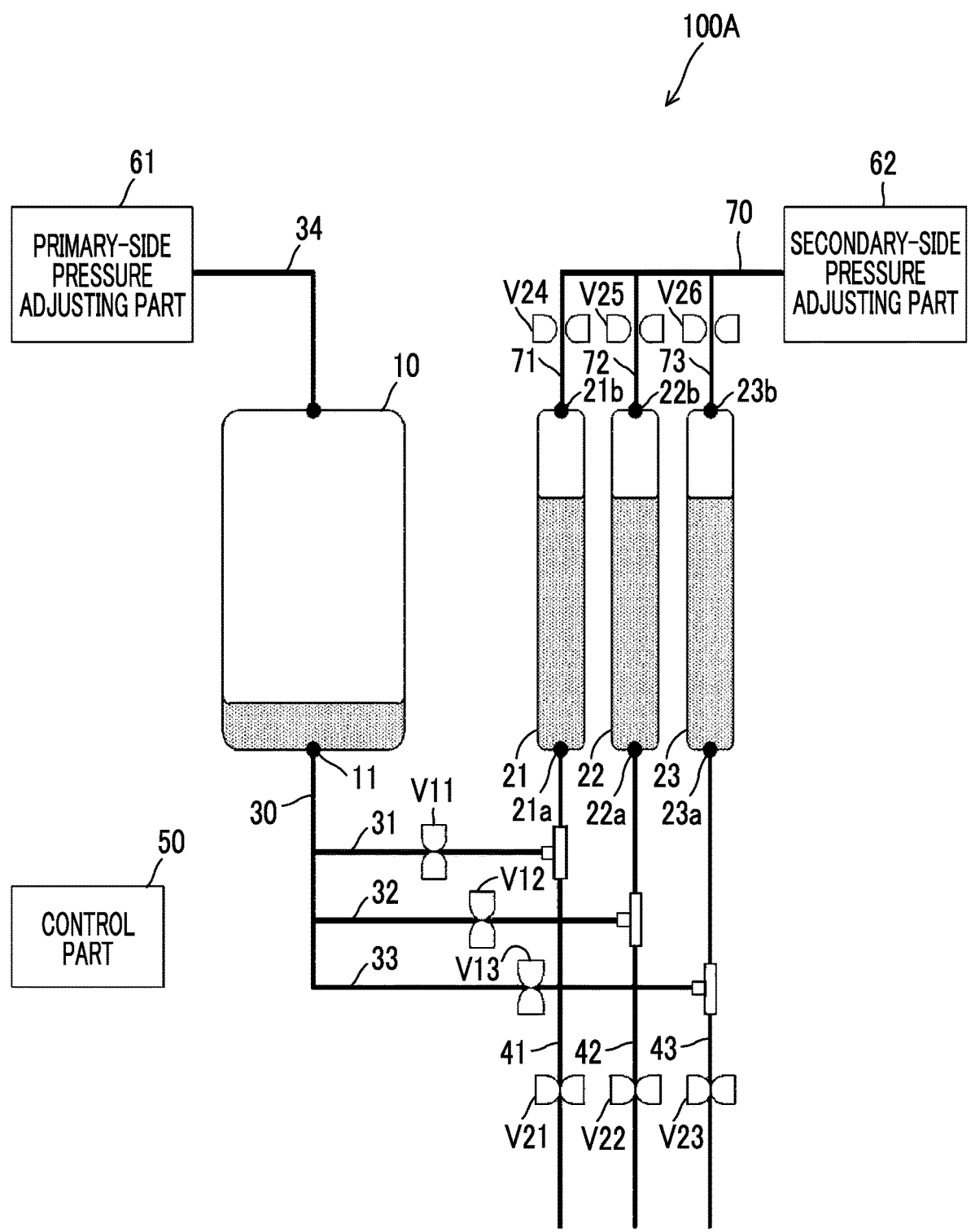
FIG. 8 is a diagram showing the state of the dispensing device in a stage where the interior of a secondary tank is opened to the atmosphere.

In step S14, the control part 50 controls the pressure adjusting valves V24, V25, and V26 to be in an open state. Thereafter, the control part 50 opens the interior of each of the secondary tanks 21, 22, and 23 to the atmosphere by controlling the secondary-side pressure adjusting part 62. FIG. 8 is a diagram showing the state of the dispensing device 100A in a stage where the processing of step S14 has been carried out.

In step S15, the control part 50 controls the discharge-side valves V21, V22, and V23 to be in an open state. In this way, the liquid accommodated in each of the secondary tanks 21, 22, and 23 is discharged to the outside of the secondary tanks 21, 22, and 23 through the secondary-side discharge flow paths 41, 42, and 43, respectively. In step S14 described previously, the interior of each of the secondary tanks 21, 22, and 23 is opened to the atmosphere, whereby the residual pressure in each of the secondary tanks 21, 22, and 23 is eliminated. In a case where the liquid discharge is performed in a state where the residual pressure in the interiors of the secondary tanks 21, 22, and 23 is excessively high, at the moment when the discharge-side valves V21, V22, and V23 have been transitioned to an open state, the liquid is vigorously discharged from each of the secondary tanks 21, 22, and 23, and thus there is a concern that a mechanical external force which is applied to the liquid may become large. According to the dispensing device 100A of this embodiment, before the liquid is discharged from each of the secondary tanks 21, 22, and 23, the interior of each of the secondary tanks 21, 22, and 23 is opened to the atmosphere. In this way, it is possible to prevent the liquid from being vigorously discharged from each of the secondary tanks 21, 22, and 23 at the moment when the discharge-side valves V21, V22, and V23 have been transitioned to an open state.

Figure 9:
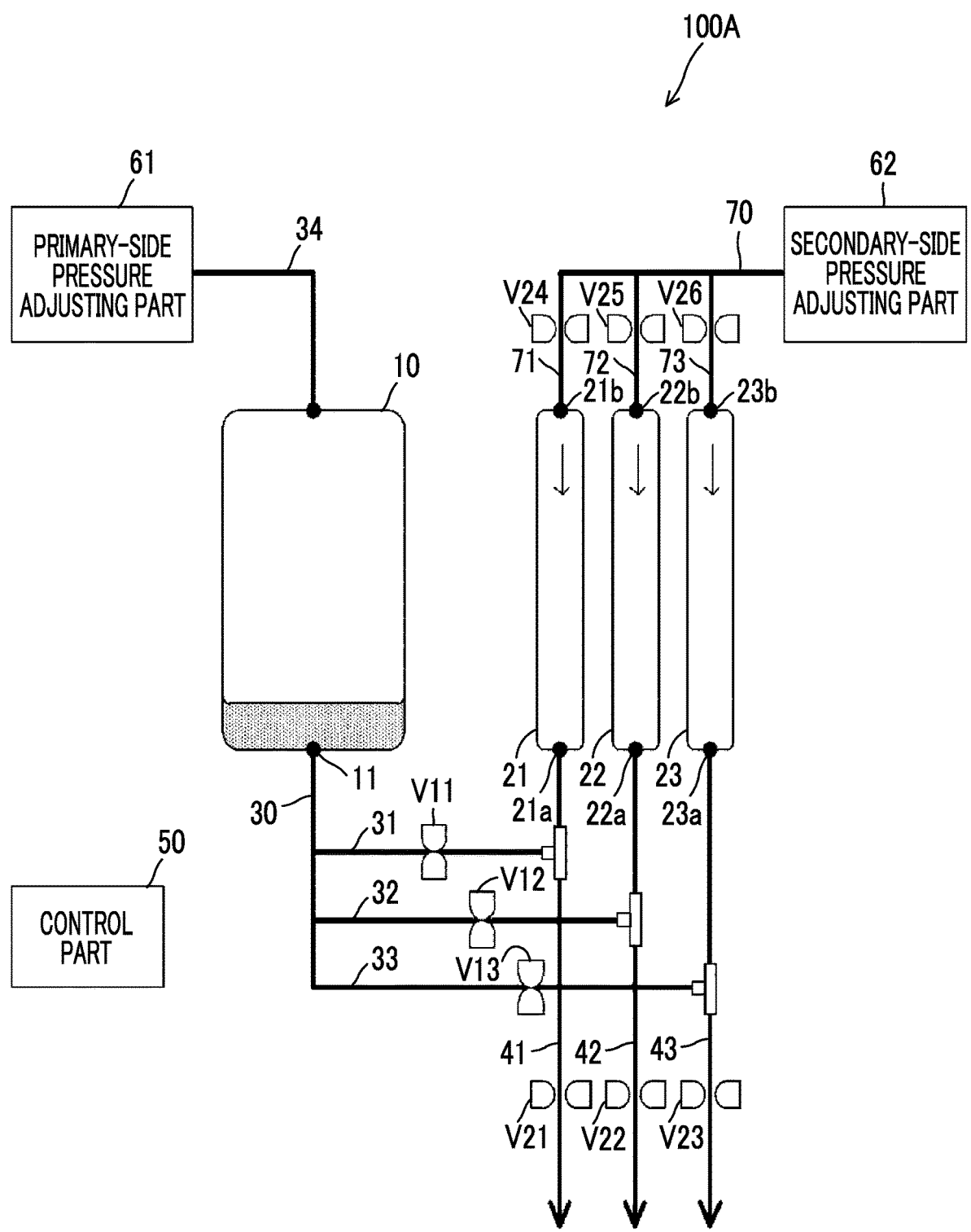
FIG. 9 is a diagram showing the state of the dispensing device in a stage of pressurizing the interior of the secondary tank.

In step S16, the control part 50 pressurizes the interior of each of the secondary tanks 21, 22, and 23 by controlling the secondary-side pressure adjusting part 62. FIG. 9 is a diagram showing the state of the dispensing device 100A in a stage where the processing of step S16 has been carried out. The discharge of the liquid to the outside of the secondary tanks 21, 22, and 23 is promoted by pressurizing the interior of each of the secondary tanks 21, 22, and 23.

As described above, according to the dispensing device 100A of this embodiment, the interior of each of the secondary tanks 21, 22, and 23 is opened to the atmosphere before the liquid is discharged from each of the secondary tanks 21, 22, and 23, and therefore, it is possible to prevent the liquid from being vigorously discharged from each of the secondary tanks 21, 22, and 23 at the moment when the discharge-side valves V21, V22, and V23 have been transitioned to an open state. In this way, in a case of discharging the liquid from the interiors of the secondary tanks 21, 22, and 23, it is possible to suppress a mechanical external force which is applied to the liquid. Further, according to the dispensing device 100A of this embodiment, the interior of each of the secondary tanks 21, 22, and 23 is pressurized after the discharge-side valves V21, V22, and V23 are transitioned to an open state, and therefore, it is possible to promote the discharge of the liquid to the outside of the secondary tanks 21, 22, and 23.

In this embodiment, a case where the secondary-side pressure adjusting part 62 is shared by the plurality of secondary tanks 21, 22, and 23 is illustrated. However, a plurality of secondary-side pressure adjusting parts may be provided corresponding to the plurality of secondary tanks 21, 22, and 23, respectively.

Third Embodiment

Figure 10:
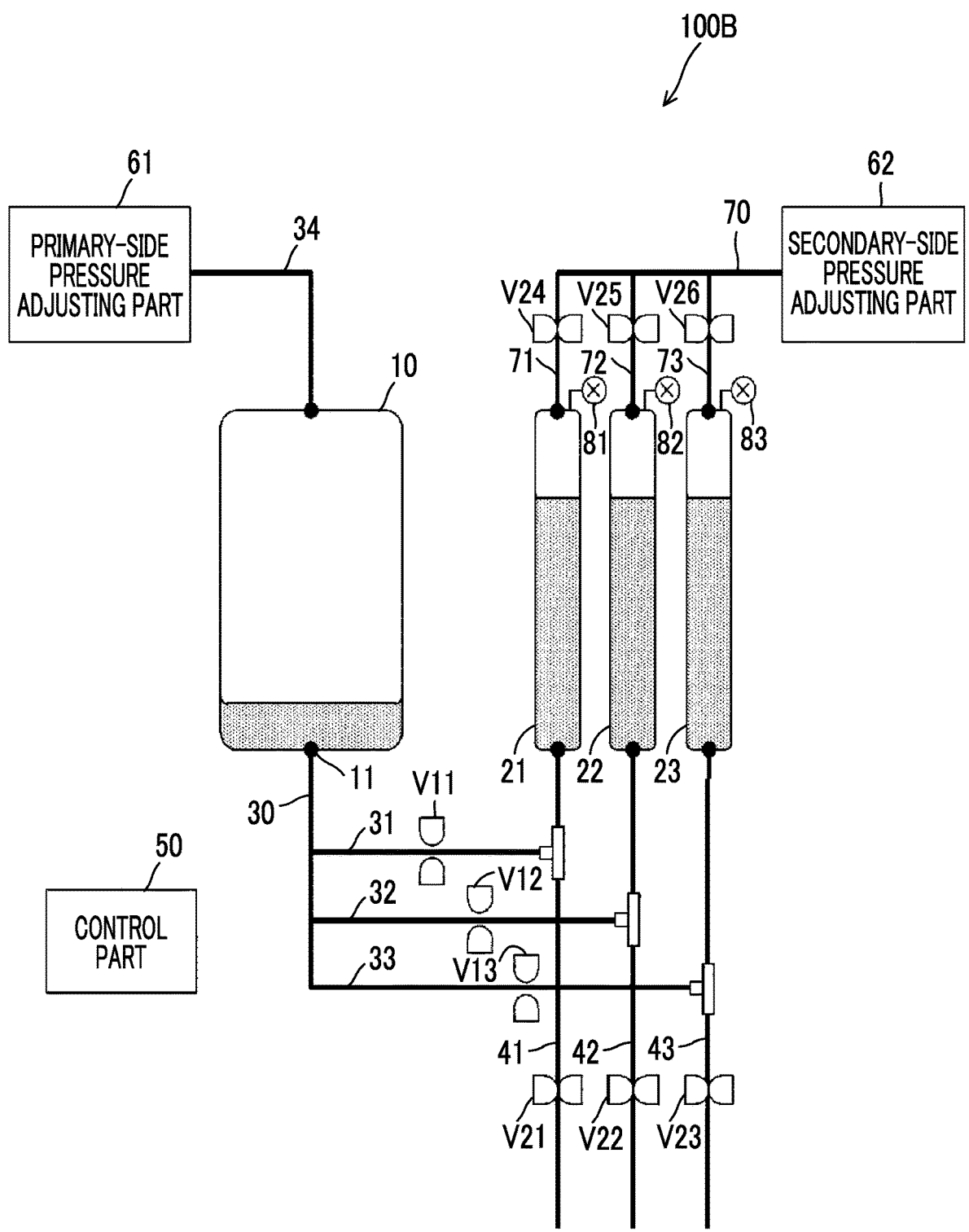
FIG. 10 is a diagram showing a configuration of a dispensing device according to another embodiment of the disclosed technique.

FIG. 10 is a diagram showing the configuration of a dispensing device 100B according to a third embodiment of the disclosed technique. The dispensing device 100B according to the third embodiment is different from the dispensing device 100A according to the second embodiment described above in that the dispensing device 100B further includes pressure sensors 81, 82, and 83.

The pressure sensors 81, 82, and 83 detect the pressures in the interiors of the secondary tanks 21, 22, and 23, respectively, and supply the detection signals indicating the detected pressures to the control part 50. The control part 50 controls the liquid transfer from the primary tank 10 to each of the secondary tanks 21, 22, and 23 by controlling the primary-side pressure adjusting part 61, the secondary-side pressure adjusting part 62, the inflow-side valves V11, V12, and V13, and the pressure adjusting valves V24, V25, and V26, based on the detection signal which is supplied from each of the pressure sensors 81, 82, and 83.

Figure 11:
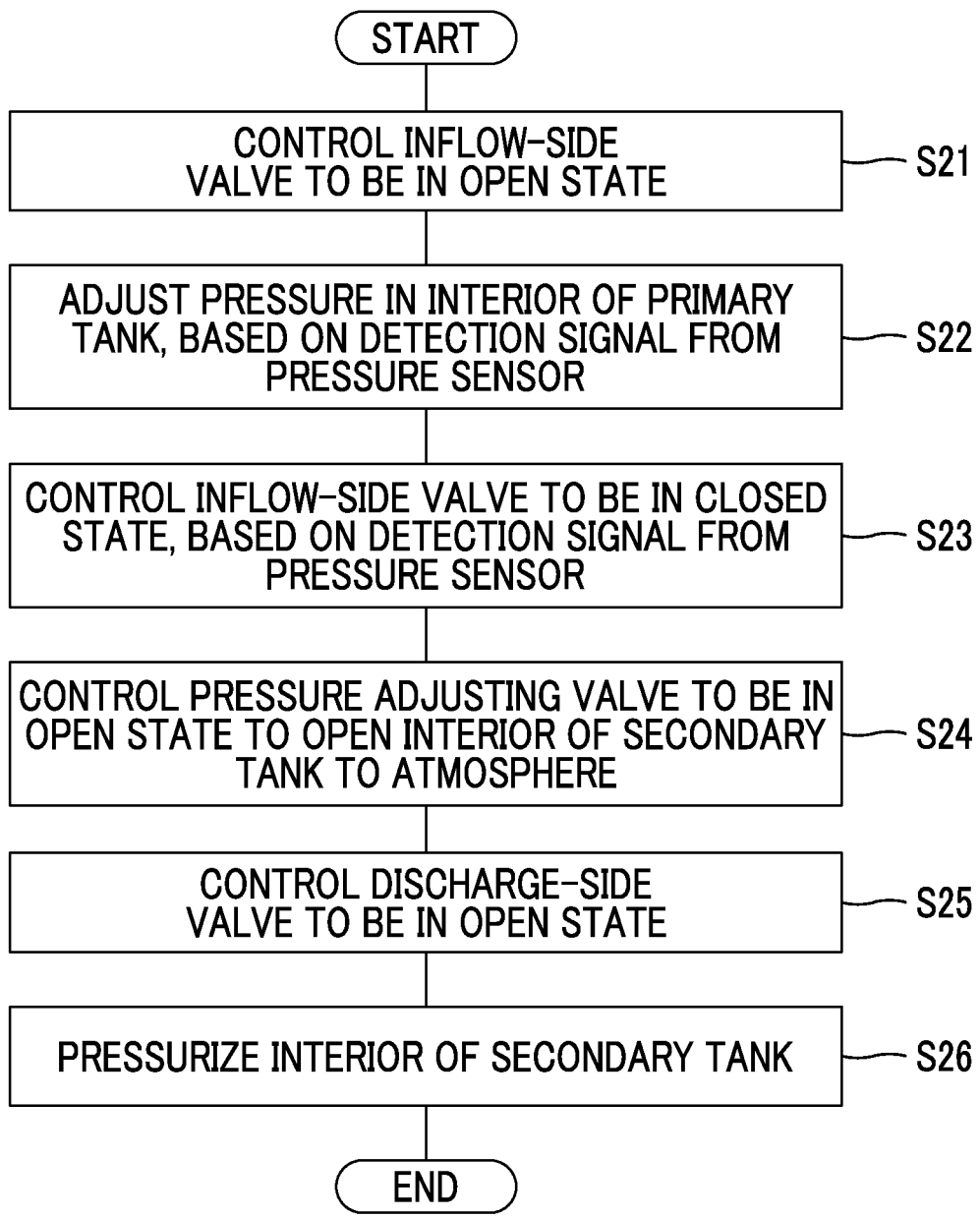
FIG. 11 is a flowchart showing a flow of processing which is carried out by the control part in a case where the dispensing device according to another embodiment of the disclosed technique performs dispensing processing.

FIG. 11 is a flowchart showing a flow of processing which is carried out by the control part 50 in a case where the dispensing device 100B performs the dispensing processing. In the initial state, it is assumed that the liquid is accommodated in the interior of the primary tank 10 and the inflow-side valves V11, V12, and V13, the discharge-side valves V21, V22, and V23, and the pressure adjusting valves V24, V25, and V26 are in a closed state.

In step S21, the control part 50 controls the inflow-side valves V11, V12, and V13 to be in an open state.

In step S22, the control part 50 pressurizes the interior of the primary tank 10 by controlling the primary-side pressure adjusting part 61. The liquid accommodated in the interior of the primary tank 10 is transferred to each of the secondary tanks 21, 22, and 23 through the branch flow paths 31, 32, and 33 by pressurizing the interior of the primary tank 10 while making the inflow-side valves V11, V12, and V13 be in an open state. The liquid is injected from the flow ports 21a, 22a, and 23a provided in the respective bottom portions of the secondary tanks 21, 22, and 23 into the respective secondary tanks 21, 22, and 23.

In this embodiment, the control part 50 increases the pressure in the interior of the primary tank 10 in stages by controlling the primary-side pressure adjusting part 61. In this way, the liquid transfer from the primary tank 10 to each of the secondary tanks 21, 22, and 23 is performed in stages, and thus the pressure in the interior of each of the secondary tanks 21, 22, and 23 also increases in stages.

Therefore, in step S22, the control part 50 adjusts the pressure in the interior of the primary tank 10 in each stage in a case of increasing the pressure in the interior of the primary tank 10 in stages, based on the detection signal which is supplied from each of the pressure sensors 81, 82, and 83. For example, the control part 50 determines the pressure in the interior of the primary tank 10 in each stage such that the average value of the pressures in the respective secondary tanks 21, 22, and 23 which are indicated by the detection signals which are supplied from the pressure sensors 81, 82, and 83 in each stage in a case of increasing the pressure in the interior of the primary tank 10 in stages becomes a predetermined value. That is, the control part 50 feedback-controls the pressure in the interior of the primary tank 10 by using the detection signals which are supplied from the pressure sensors 81, 82, and 83.

In step S23, the control part 50 individually controls the inflow-side valves V11, V12, and V13 to be in a closed state, based on the detection signals which are supplied from the pressure sensors 81, 82, and 83. For example, the control part 50 controls the inflow-side valve corresponding to the secondary tank determined that the amount of accommodated liquid which is estimated from the pressures detected by the pressure sensors 81, 82, and 83 has reached a predetermined amount, among the secondary tanks 21, 22, and 23, to be in a closed state. For example, the control part 50 completes the liquid transfer to the secondary tank 21 by controlling the inflow-side valve V11 to be in a closed state, in a case where a determination that the amount of the liquid accommodated in the secondary tank 21 has reached a predetermined amount is made based on the detection signal which is supplied from the pressure sensor 81.

In a case where the transfer of a predetermined amount of liquid to each of the secondary tanks 21, 22, and 23 is completed, in step S24, the control part 50 controls the pressure adjusting valves V24, V25, and V26 to be in an open state. Thereafter, the control part 50 opens the interior of each of the secondary tanks 21, 22, and 23 to the atmosphere by controlling the secondary-side pressure adjusting part 62.

In step S25, the control part 50 controls the discharge-side valves V21, V22, and V23 to be in an open state. In this way, the liquid accommodated in each of the secondary tanks 21, 22, and 23 is discharged to the outside of the secondary tanks 21, 22, and 23 through the secondary-side discharge flow paths 41, 42, and 43, respectively.

In step S26, the control part 50 pressurizes the interior of each of the secondary tanks 21, 22, and 23 by controlling the secondary-side pressure adjusting part 62. In this way, the discharge of the liquid to the outside of the secondary tanks 21, 22, and 23 is promoted.

As described above, according to the dispensing device 100B of this embodiment, the pressure in the primary tank 10 is adjusted based on the detection signals which are supplied from the pressure sensors 81, 82, and 83 provided in the secondary tanks 21, 22, and 23, respectively. In this way, the liquid transfer from the primary tank 10 to each of the secondary tanks 21, 22, and 23 can be performed more controllably. For example, it is also possible to more precisely control the flow velocity of the liquid which is transferred from the primary tank 10 to each of the secondary tanks 21, 22, and 23.

Further, according to the dispensing device 100B of this embodiment, the inflow-side valve corresponding to the secondary tank determined that the amount of accommodated liquid which is estimated from the pressures detected by the pressure sensors 81, 82, and 83, among the secondary tanks 21, 22, and 23, has reached a predetermined amount, is controlled to be in a closed state. In this manner, by individually controlling timings of making the inflow-side valves V11, V12, and V13 be in a closed state, based on the pressures detected by the pressure sensors 81, 82, and 83, it is possible to further enhance the uniformity of the amount of the liquid which is accommodated in each of the secondary tanks 21, 22, and 23.

Figure 12:
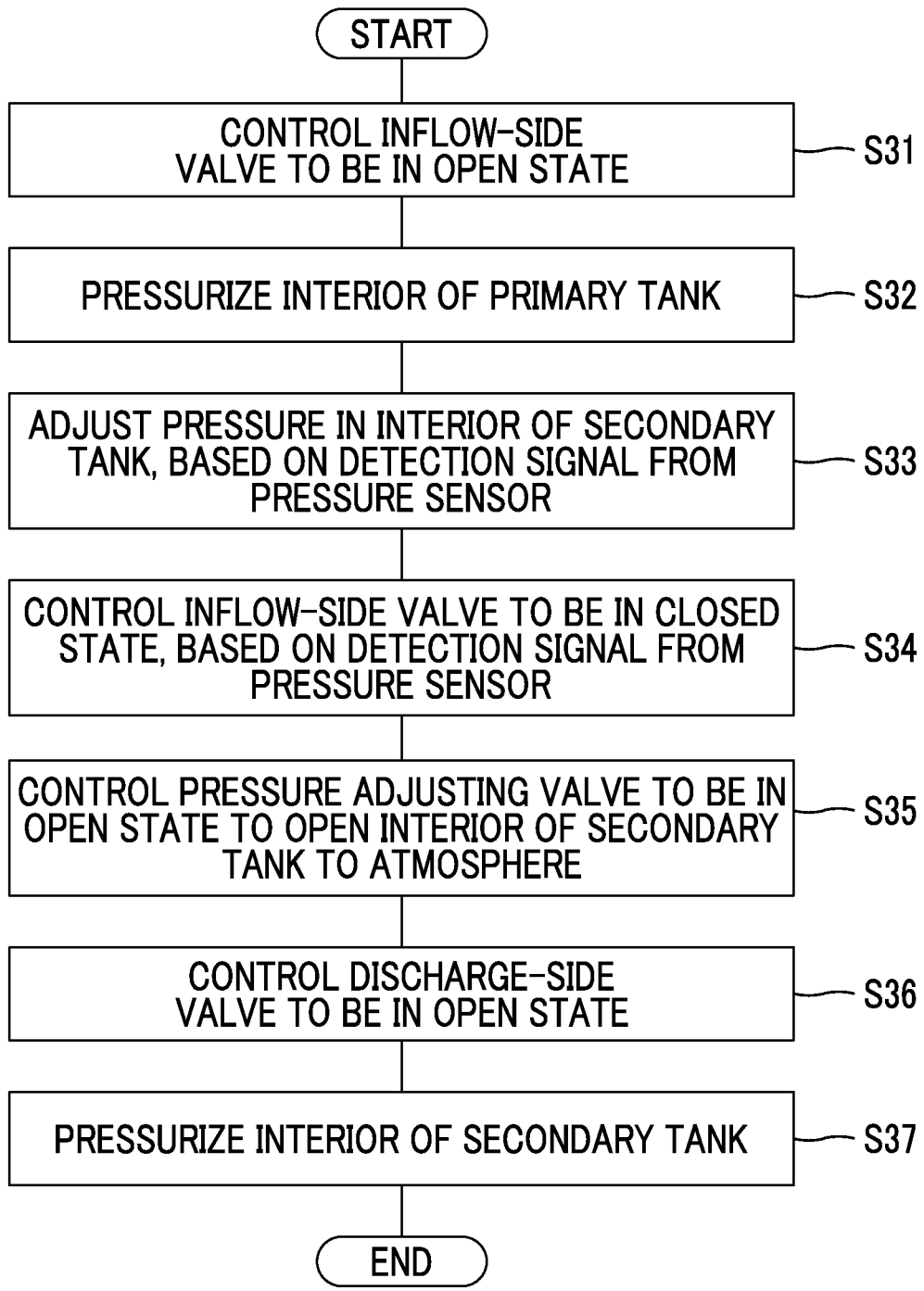
FIG. 12 is a flowchart showing a flow of processing which is carried out by the control part in a case where the dispensing device according to another embodiment of the disclosed technique performs dispensing processing.

FIG. 12 is a flowchart showing another example of the flow of the processing which is carried out by the control part 50 in a case where the dispensing device 100B performs the dispensing processing. In the initial state, it is assumed that the liquid is accommodated in the interior of the primary tank 10 and the inflow-side valves V11, V12, and V13, the discharge-side valves V21, V22, and V23, and the pressure adjusting valves V24, V25, and V26 are in a closed state.

In step S31, the control part 50 controls the inflow-side valves V11, V12, and V13 to be in an open state.

In step S32, the control part 50 pressurizes the interior of the primary tank 10 by controlling the primary-side pressure adjusting part 61. The liquid accommodated in the interior of the primary tank 10 is transferred to each of the secondary tanks 21, 22, and 23 through the branch flow paths 31, 32, and 33 by pressurizing the interior of the primary tank 10 while making the inflow-side valves V11, V12, and V13 be in an open state. The liquid is injected from the flow ports 21a, 22a, and 23a provided in the respective bottom portions of the secondary tanks 21, 22, and 23 into the respective secondary tanks 21, 22, and 23.

In this embodiment, the control part 50 increases the pressure in the interior of the primary tank 10 in stages by controlling the primary-side pressure adjusting part 61. In this way, the liquid transfer from the primary tank 10 to each of the secondary tanks 21, 22, and 23 is performed in stages, and thus the pressure in the interior of each of the secondary tanks 21, 22, and 23 also increases in stages.

In step S33, the control part 50 controls the pressure adjusting valves V24, V25, and V26 to be in an open state, and adjusts the pressure in the interior of each of the secondary tanks 21, 22, and 23 by controlling the secondary-side pressure adjusting part 62, based on the detection signal which is supplied from each of the pressure sensors 81, 82, and 83.

That is, in each stage where the stepwise liquid transfer is performed from the primary tank 10 to each of the secondary tanks 21, 22, and 23, the secondary-side pressure adjusting part 62 changes the pressure in the interior of each of the secondary tanks 21, 22, and 23 as follows, under the control of the control part 50.

The secondary-side pressure adjusting part 62 decompresses the interior of the secondary tank determined that the amount of accommodated liquid which is estimated from the pressures detected by the pressure sensors 81, 82, and 83 is smaller than a reference liquid amount determined for each stage in a case of increasing the pressure in the interior of the primary tank 10 in stages, among the secondary tanks 21, 22, and 23. In this way, the liquid transfer to the secondary tank determined that the amount of accommodated liquid is smaller than the reference liquid amount is promoted.

On the other hand, the secondary-side pressure adjusting part 62 pressurizes the interior of the secondary tank determined that the amount of accommodated liquid which is estimated from the pressures detected by the pressure sensors 81, 82, and 83 is larger than the reference liquid amount, among the secondary tanks 21, 22, and 23. In this way, the liquid transfer to the secondary tank determined that the amount of accommodated liquid is larger than the reference liquid amount is suppressed.

In step S34, the control part 50 individually controls the inflow-side valves V11, V12, and V13 to be in a closed state, based on the detection signals which are supplied from the pressure sensors 81, 82, and 83. For example, the control part 50 controls the inflow-side valve corresponding to the secondary tank determined that the amount of accommodated liquid which is estimated from the pressures detected by the pressure sensors 81, 82, and 83 has reached a predetermined amount, among the secondary tanks 21, 22, and 23, to be in a closed state.

In a case where the transfer of a predetermined amount of liquid to each of the secondary tanks 21, 22, and 23 is completed, in step S35, the control part 50 opens the interior of each of the secondary tanks 21, 22, and 23 to the atmosphere by controlling the secondary-side pressure adjusting part 62.

In step S36, the control part 50 controls the discharge-side valves V21, V22, and V23 to be in an open state. In this way, the liquid accommodated in each of the secondary tanks 21, 22, and 23 is discharged to the outside of the secondary tanks 21, 22, and 23 through the secondary-side discharge flow paths 41, 42, and 43, respectively.

In step S37, the control part 50 pressurizes the interior of each of the secondary tanks 21, 22, and 23 by controlling the secondary-side pressure adjusting part 62. In this way, the discharge of the liquid to the outside of the secondary tanks 21, 22, and 23 is promoted.

As described above, in a case where the liquid is transferred from the primary tank 10 to each of the secondary tanks 21, 22, and 23, by adjusting the pressure in the interior of each of the secondary tanks 21, 22, and 23, based on the detection signal which is supplied from each of the pressure sensors 81, 82, and 83, it is possible to further enhance the uniformity of the amount of liquid which is accommodated in each of the secondary tanks 21, 22, and 23.

In this embodiment, a case where the pressure sensors 81, 82, and 83 are respectively provided in the secondary tanks 21, 22, and 23 has been illustrated. However, a pressure sensor may be provided in any one of the secondary tanks 21, 22, or 23. In this case, a pressure value which is indicated by the detection signal of the one pressure sensor is used as a representative value representing a pressure value in the interior of each of the secondary tanks 21, 22, and 23. According to the dispensing device 100B of this embodiment, while the liquid is being transferred from the primary tank 10 to each of the secondary tanks 21, 22, and 23, the pressures in the interiors of the secondary tanks 21, 22, and 23 have approximately the same magnitude, and therefore, it is possible to use the pressure value which is indicated by the detection signal of one pressure sensor as a representative value. In a case of using one pressure sensor, in step S22 of the processing shown in FIG. 11, the pressure in the interior of the primary tank 10 is adjusted based on this representative value. In step S23 of the processing shown in FIG. 11 and step S34 of the processing shown in FIG. 12, the inflow-side valves V11, V12, and V13 are controlled to be in a closed state at the same time, based on this representative value. In step S33 of the processing shown in FIG. 12, the pressure in the interior of each of the secondary tanks 21, 22, and 23 is adjusted based on this representative value.

Fourth Embodiment

Figure 13:
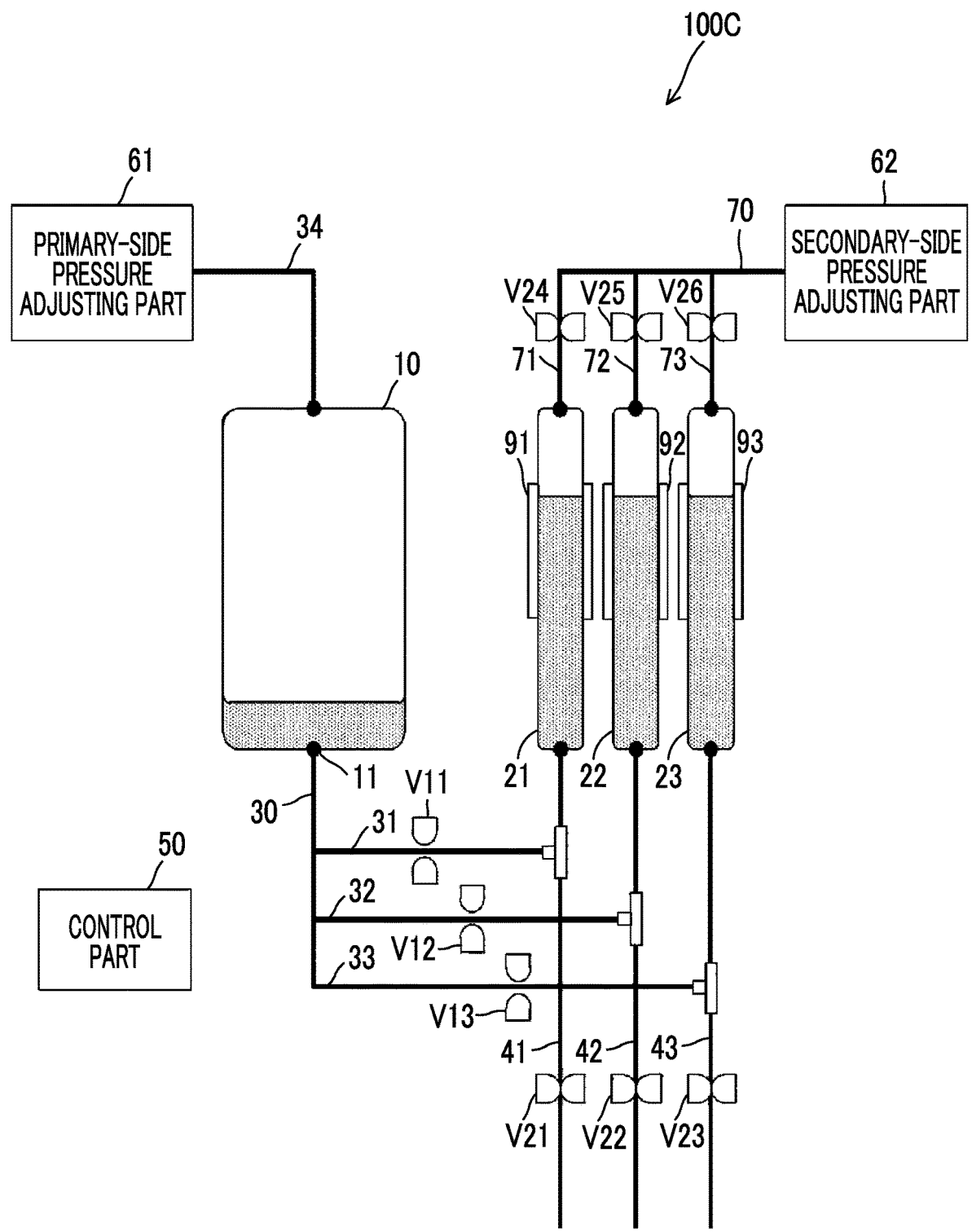
FIG. 13 is a diagram showing a configuration of a dispensing device according to another embodiment of the disclosed technique.

FIG. 13 is a diagram showing the configuration of a dispensing device 100C according to a fourth embodiment of the disclosed technique. The dispensing device 100C according to the fourth embodiment is different from the dispensing device 100A according to the second embodiment in that the dispensing device 100C further includes level sensors 91, 92, and 93. In other words, the dispensing device 100C has a configuration in which the pressure sensors 81, 82, and 83 in the dispensing device 100B according to the third embodiment are replaced with the level sensors 91, 92, and 93.

The level sensors 91, 92, and 93 detect the heights of the liquid levels of the liquids accommodated in the secondary tanks 21, 22, and 23, respectively, and supply detection signals indicating the detected liquid level heights to the control part 50. The control part 50 controls the liquid transfer from the primary tank 10 to each of the secondary tanks 21, 22, and 23 by controlling the primary-side pressure adjusting part 61, the secondary-side pressure adjusting part 62, the inflow-side valves V11, V12, and V13, and the pressure adjusting valves V24, V25, and V26, based on the detection signal which is supplied from each of the level sensors 91, 92, and 93.

Figure 14:
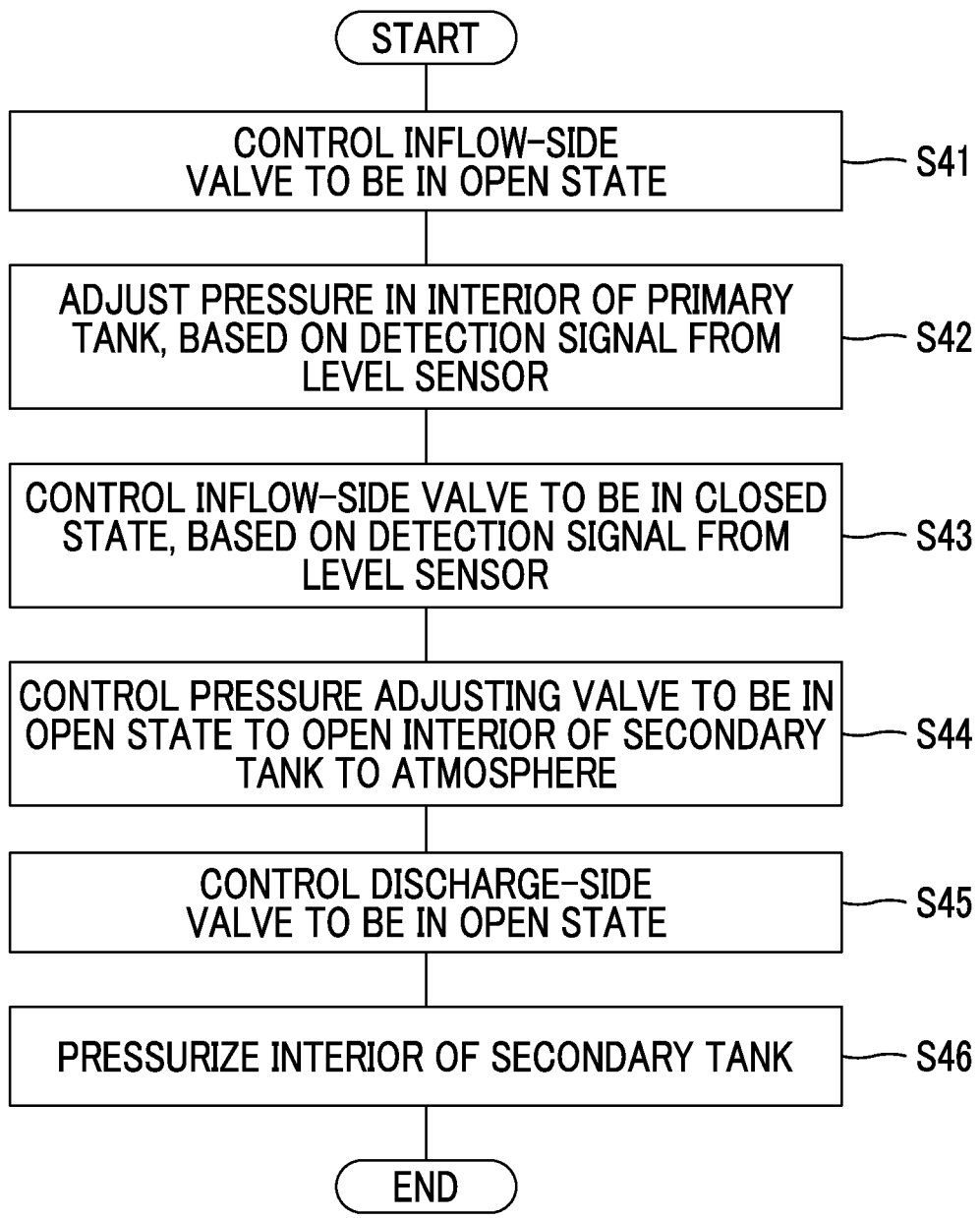
FIG. 14 is a flowchart showing a flow of processing which is carried out by the control part in a case where the dispensing device according to another embodiment of the disclosed technique performs dispensing processing.

FIG. 14 is a flowchart showing the flow of the processing which is carried out by the control part 50 in a case where the dispensing device 100C performs the dispensing processing. In the initial state, it is assumed that the liquid is accommodated in the interior of the primary tank 10 and the inflow-side valves V11, V12, and V13, the discharge-side valves V21, V22, and V23, and the pressure adjusting valves V24, V25, and V26 are in a closed state.

In step S41, the control part 50 controls the inflow-side valves V11, V12, and V13 to be in an open state.

In step S42, the control part 50 pressurizes the interior of the primary tank 10 by controlling the primary-side pressure adjusting part 61. The liquid accommodated in the interior of the primary tank 10 is transferred to each of the secondary tanks 21, 22, and 23 through the branch flow paths 31, 32, and 33 by pressurizing the interior of the primary tank 10 while making the inflow-side valves V11, V12, and V13 be in an open state. The liquid is injected from the flow ports 21a, 22a, and 23a provided in the respective bottom portions of the secondary tanks 21, 22, and 23 into the respective secondary tanks 21, 22, and 23.

In this embodiment, the control part 50 increases the pressure in the interior of the primary tank 10 in stages by controlling the primary-side pressure adjusting part 61. In this way, the liquid transfer from the primary tank 10 to each of the secondary tanks 21, 22, and 23 is performed in stages, and thus the pressure in the interior of each of the secondary tanks 21, 22, and 23 also increases in stages.

Therefore, in step S42, the control part 50 adjusts the pressure in the interior of the primary tank 10 in each stage in a case of increasing the pressure in the interior of the primary tank 10 in stages, based on the detection signal which is supplied from each of the level sensors 91, 92, and 93. For example, the control part 50 determines the pressure in the interior of the primary tank 10 in each stage such that the average value of the heights of the liquid levels of the respective secondary tanks 21, 22, and 23 which are indicated by the detection signals which are supplied from the level sensors 91, 92, and 93 in each stage in a case of increasing the pressure in the interior of the primary tank 10 in stages becomes a predetermined value. That is, the control part 50 feedback-controls the pressure in the interior of the primary tank 10 by using the detection signals which are supplied from the level sensors 91, 92, and 93.

In step S43, the control part 50 individually controls the inflow-side valves V11, V12, and V13 to be in a closed state, based on the detection signals which are supplied from the level sensors 91, 92, and 93. For example, the control part 50 controls the inflow-side valve corresponding to the secondary tank determined that the amount of accommodated liquid which is estimated from the liquid level heights detected by the level sensors 91, 92, and 93 has reached a predetermined amount, among the secondary tanks 21, 22, and 23, to be in a closed state.

In a case where the transfer of a predetermined amount of liquid to each of the secondary tanks 21, 22, and 23 is completed, in step S44, the control part 50 controls the pressure adjusting valves V24, V25, and V26 to be in an open state. Thereafter, the control part 50 opens the interior of each of the secondary tanks 21, 22, and 23 to the atmosphere by controlling the secondary-side pressure adjusting part 62.

In step S45, the control part 50 controls the discharge-side valves V21, V22, and V23 to be in an open state. In this way, the liquid accommodated in each of the secondary tanks 21, 22, and 23 is discharged to the outside of the secondary tanks 21, 22, and 23 through the secondary-side discharge flow paths 41, 42, and 43, respectively.

In step S46, the control part 50 pressurizes the interior of each of the secondary tanks 21, 22, and 23 by controlling the secondary-side pressure adjusting part 62. In this way, the discharge of the liquid to the outside of the secondary tanks 21, 22, and 23 is promoted.

As described above, according to the dispensing device 100C of this embodiment, the pressure in the primary tank 10 is adjusted based on the detection signals which are supplied from the level sensors 91, 92, and 93 provided in the secondary tanks 21, 22, and 23, respectively. In this way, the liquid transfer from the primary tank 10 to each of the secondary tanks 21, 22, and 23 can be performed more controllably. For example, it is also possible to more precisely control the flow velocity of the liquid which is transferred from the primary tank 10 to each of the secondary tanks 21, 22, and 23.

Further, according to the dispensing device 100C of this embodiment, the inflow-side valve corresponding to the secondary tank determined that the amount of accommodated liquid which is estimated from the liquid level heights detected by the level sensors 91, 92, and 93, among the secondary tanks 21, 22, and 23, has reached a predetermined amount, is controlled to be in a closed state. In this manner, by individually controlling timings of making the inflow-side valves V11, V12, and V13 be in a closed state, based on the liquid level heights detected by the level sensors 91, 92, and 93, it is possible to further enhance the uniformity of the amount of the liquid which is accommodated in each of the secondary tanks 21, 22, and 23.

Figure 15:
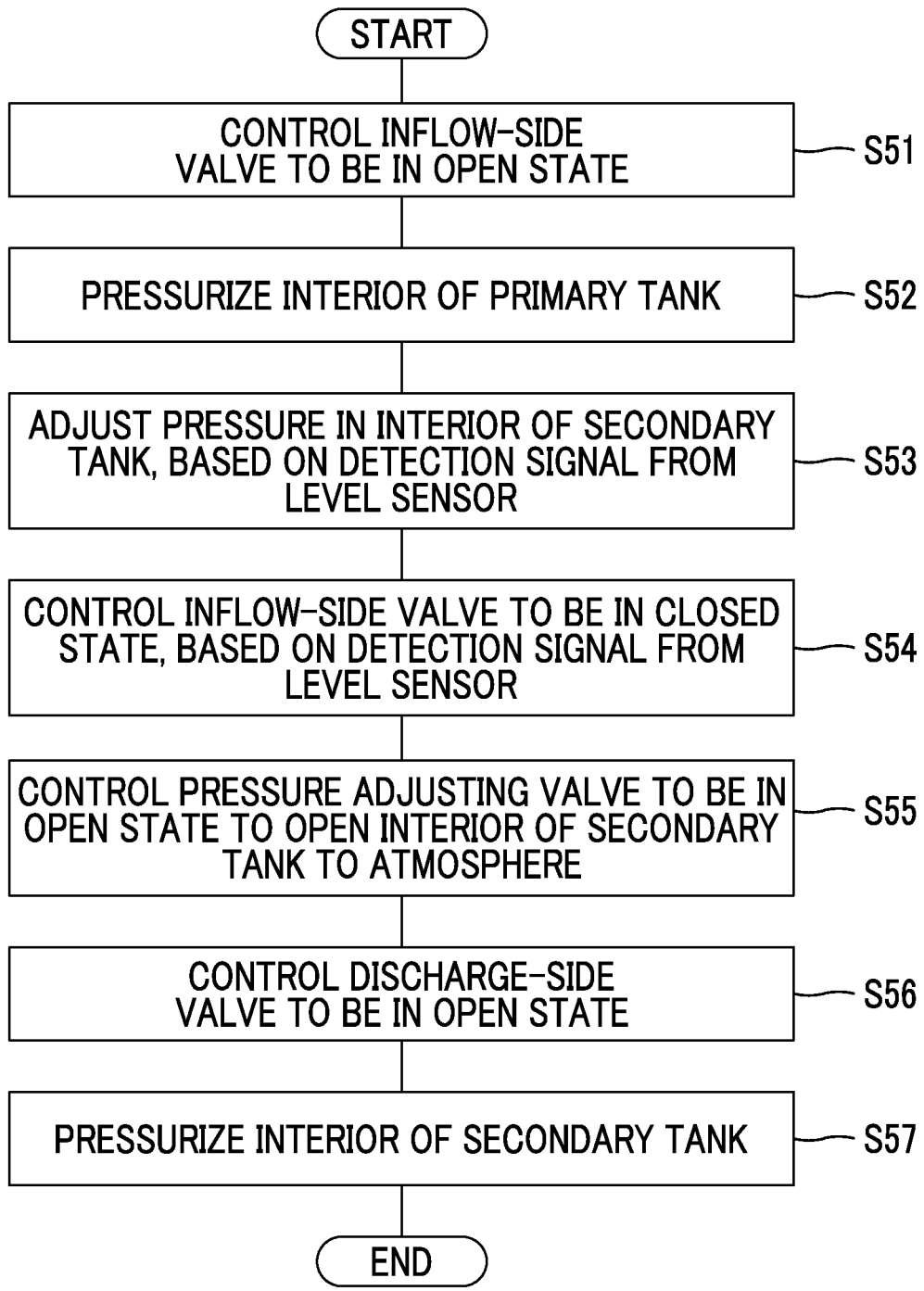
FIG. 15 is a flowchart showing a flow of processing which is carried out by the control part in a case where the dispensing device according to another embodiment of the disclosed technique performs dispensing processing.

FIG. 15 is a flowchart showing another example of the flow of the processing which is carried out by the control part 50 in a case where the dispensing device 100C performs the dispensing processing. In the initial state, it is assumed that the liquid is accommodated in the interior of the primary tank 10 and the inflow-side valves V11, V12, and V13, the discharge-side valves V21, V22, and V23, and the pressure adjusting valves V24, V25, and V26 are in a closed state.

In step S51, the control part 50 controls the inflow-side valves V11, V12, and V13 to be in an open state.

In step S52, the control part 50 pressurizes the interior of the primary tank 10 by controlling the primary-side pressure adjusting part 61. The liquid accommodated in the interior of the primary tank 10 is transferred to each of the secondary tanks 21, 22, and 23 through the branch flow paths 31, 32, and 33 by pressurizing the interior of the primary tank 10 while making the inflow-side valves V11, V12, and V13 be in an open state. The liquid is injected from the flow ports 21a, 22a, and 23a provided in the respective bottom portions of the secondary tanks 21, 22, and 23 into the respective secondary tanks 21, 22, and 23.

In this embodiment, the control part 50 increases the pressure in the interior of the primary tank 10 in stages by controlling the primary-side pressure adjusting part 61. In this way, the liquid transfer from the primary tank 10 to each of the secondary tanks 21, 22, and 23 is performed in stages, and thus the pressure in the interior of each of the secondary tanks 21, 22, and 23 also increases in stages.

In step S53, the control part 50 controls the pressure adjusting valves V24, V25, and V26 to be in an open state, and adjusts the pressure in the interior of each of the secondary tanks 21, 22, and 23 by controlling the secondary-side pressure adjusting part 62, based on the detection signal which is supplied from each of the level sensors 91, 92, and 93.

That is, in each stage where the stepwise liquid transfer is performed from the primary tank 10 to each of the secondary tanks 21, 22, and 23, the secondary-side pressure adjusting part 62 changes the pressure in the interior of each of the secondary tanks 21, 22, and 23 as follows, under the control of the control part 50.

The secondary-side pressure adjusting part 62 decompresses the interior of the secondary tank determined that the amount of accommodated liquid which is estimated from the liquid level heights detected by the level sensors 91, 92, and 93 is smaller than the reference liquid amount determined for each stage in a case of increasing the pressure in the interior of the primary tank 10 in stages, among the secondary tanks 21, 22, and 23. In this way, the liquid transfer to the secondary tank determined that the amount of accommodated liquid is smaller than the reference liquid amount is promoted.

On the other hand, the secondary-side pressure adjusting part 62 pressurizes the interior of the secondary tank determined that the amount of accommodated liquid which is estimated from the liquid level heights detected by the level sensors 91, 92, and 93 is larger than the reference liquid amount, among the secondary tanks 21, 22, and 23. In this way, the liquid transfer to the secondary tank determined that the amount of accommodated liquid is larger than the reference liquid amount is suppressed.

In step S54, the control part 50 individually controls the inflow-side valves V11, V12, and V13 to be in a closed state, based on the detection signals which are supplied from the level sensors 91, 92, and 93. For example, the control part 50 controls the inflow-side valve corresponding to the secondary tank determined that the amount of accommodated liquid which is estimated from the liquid level heights detected by the level sensors 91, 92, and 93 has reached a predetermined amount, among the secondary tanks 21, 22, and 23, to be in a closed state.

In a case where the transfer of a predetermined amount of liquid to each of the secondary tanks 21, 22, and 23 is completed, in step S55, the control part 50 opens the interior of each of the secondary tanks 21, 22, and 23 to the atmosphere by controlling the secondary-side pressure adjusting part 62.

In step S56, the control part 50 controls the discharge-side valves V21, V22, and V23 to be in an open state. In this way, the liquid accommodated in each of the secondary tanks 21, 22, and 23 is discharged to the outside of the secondary tanks 21, 22, and 23 through the secondary-side discharge flow paths 41, 42, and 43, respectively.

In step S57, the control part 50 pressurizes the interior of each of the secondary tanks 21, 22, and 23 by controlling the secondary-side pressure adjusting part 62. In this way, the discharge of the liquid to the outside of the secondary tanks 21, 22, and 23 is promoted.

As described above, in a case where the liquid is transferred from the primary tank 10 to each of the secondary tanks 21, 22, and 23, by adjusting the pressure in the interior of each of the secondary tanks 21, 22, and 23, based on the detection signal which is supplied from each of the level sensors 91, 92, and 93, it is possible to further enhance the uniformity of the amount of liquid which is accommodated in each of the secondary tanks 21, 22, and 23.

In this embodiment, a case where the level sensors 91, 92, and 93 are respectively provided in the secondary tanks 21, 22, and 23 has been illustrated. However, a level sensor may be provided in any one of the secondary tanks 21, 22, or 23. In this case, the height of the liquid level which is indicated by the detection signal of the one level sensor is used as a representative value representing the height of the liquid level in each of the secondary tanks 21, 22, and 23. According to the dispensing device 100C of this embodiment, while the liquid is being transferred from the primary tank 10 to each of the secondary tanks 21, 22, and 23, the height of the liquid level of the liquid which is accommodated in each of the interiors of the secondary tanks 21, 22, and 23 rises approximately equally, and therefore, it is possible to use the height of the liquid level which is indicated by the detection signal of one level sensor as a representative value. In a case of using one level sensor, in step S42 of the processing shown in FIG. 14, the pressure in the interior of the primary tank 10 is adjusted based on this representative value. In step S43 of the processing shown in FIG. 14 and step S54 of the processing shown in FIG. 15, the inflow-side valves V11, V12, and V13 are controlled to be in a closed state at the same time, based on this representative value. In step S53 of the processing shown in FIG. 15, the pressure in the interior of each of the secondary tanks 21, 22, and 23 is adjusted based on this representative value.

Fifth Embodiment

Figure 16:
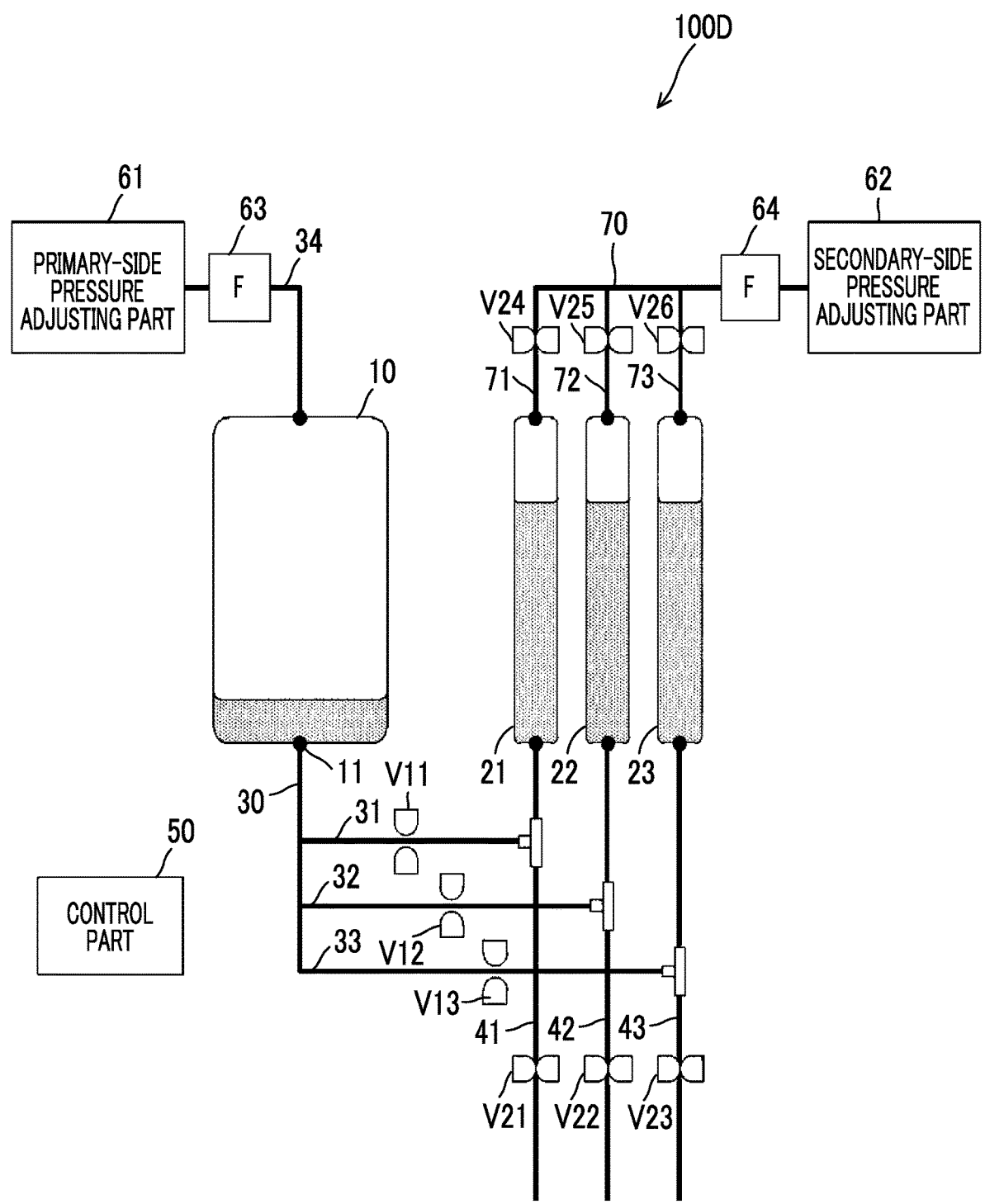
FIG. 16 is a diagram showing a configuration of a dispensing device according to another embodiment of the disclosed technique.

FIG. 16 is a diagram showing the configuration of a dispensing device 100D according to a fifth embodiment of the disclosed technique. The dispensing device 100D is different from the dispensing device 100A according to the second embodiment described above in that the dispensing device 100D further includes a first filter 63 and a second filter 64.

The first filter 63 is provided in the middle of the pipe 34 which connects the primary-side pressure adjusting part 61 and the primary tank 10. The first filter 63 suppresses inflow of unnecessary components contained in a gas which is supplied from the primary-side pressure adjusting part 61 to the primary tank 10 into the interior of the primary tank 10, in a case where the primary-side pressure adjusting part 61 pressurizes the interior of the primary tank 10. In a case where the liquid which is accommodated in the primary tank 10 is, for example, a cell suspension, the first filter 63 may be a sterile filter.

The second filter 64 is provided in the middle of the common pipe 70 which connects the secondary-side pressure adjusting part 62 and the secondary tanks 21, 22, and 23. The second filter 64 suppresses inflow of unnecessary components contained in a gas which is supplied from the secondary-side pressure adjusting part 62 to the secondary tanks 21, 22, and 23 into the interiors of the secondary tanks 21, 22, and 23, in a case where the secondary-side pressure adjusting part 62 pressurizes the interiors of the secondary tanks 21, 22, and 23. In a case where the liquid which is accommodated in the secondary tanks 21, 22, and 23 is, for example, a cell suspension, the second filter 64 may be a sterile filter.

As described above, according to the dispensing device 100D of this embodiment, since the first filter 63 is provided in the middle of the pipe 34 and the second filter 64 is provided in the middle of the common pipe 70, it is possible to suppress the inflow of unnecessary components into the interior of each of the primary tank 10 and the secondary tanks 21, 22, and 23.

Sixth Embodiment

Figure 17:
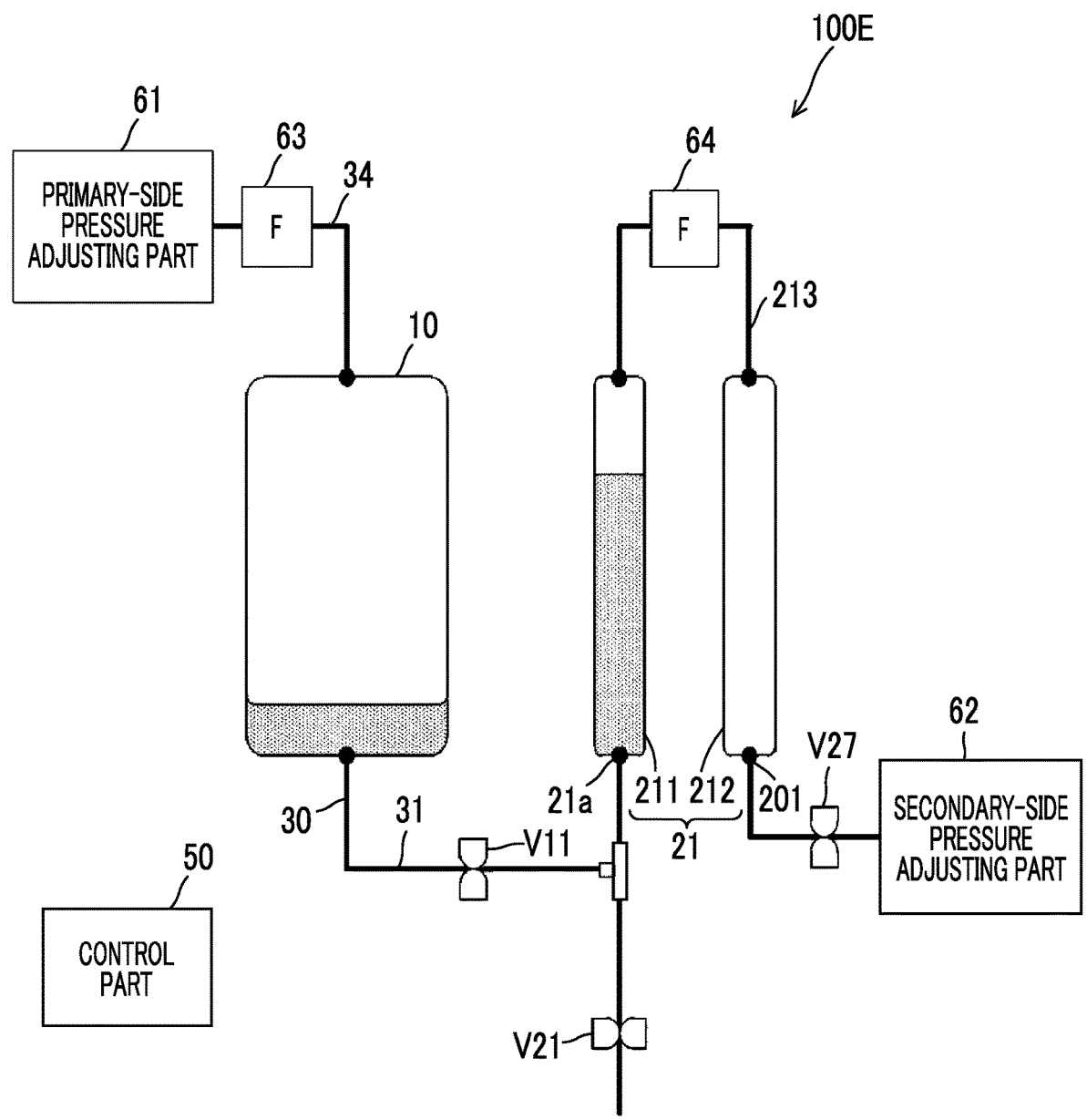
FIG. 17 is a diagram showing a configuration of a dispensing device according to another embodiment of the disclosed technique.

FIG. 17 is a diagram showing the configuration of a dispensing device 100E according to a sixth embodiment of the disclosed technique. In the dispensing device 100E, the configuration of the secondary tank and the disposition of the second filter 64 are different from those in the dispensing device 100D according to the fifth embodiment described above. In FIG. 17, only one secondary tank 21 is shown. However, other secondary tanks which are not shown in the drawing also have the same configuration as the secondary tank 21.

In the dispensing device 100E according to this embodiment, the secondary tank 21 is configured to include a first portion 211 and a second portion 212. The first portion 211 is a portion which accommodates the liquid which is transferred from the primary tank 10. The second portion 212 is connected to the first portion 211 through a connection pipe 213. The second portion 212 has a gas flow port 201 into which the gas which is supplied from the secondary-side pressure adjusting part 62 flows.

The first portion 211 and the second portion 212 communicate with each other through the connection pipe 213. Therefore, the gas which is supplied from the secondary-side pressure adjusting part 62 can flow into not only the second portion 212 but also the first portion 211 through the connection pipe 213. On the other hand, in the dispensing device 100E according to this embodiment, the liquid which is injected into the first portion 211 through the flow port 21a is sent at a liquid amount which does not flow into the second portion 212.

The second filter 64 is provided in the middle of the flow path of the connection pipe 213. The second filter 64 suppresses inflow of unnecessary components contained in the gas which is supplied from the secondary-side pressure adjusting part 62 to the first portion 211 and the second portion 212 into the first portion 211, in a case where the secondary-side pressure adjusting part 62 pressurizes the interiors of the first portion 211 and the second portion 212 of the secondary tank 21.

According to the dispensing device 100E of this embodiment, it is possible to suppress the inflow of unnecessary components into the interiors of the primary tank 10 and the first portion 211 of the secondary tank 21.

Here, in a case of performing the liquid transfer to the secondary tank with a relatively small pressure, it is necessary to increase the volume of the secondary tank to some extent to secure the amount of the gas in the interior of the secondary tank. However, in a case where the liquid which is accommodated in the secondary tank is, for example, a cell suspension, it is necessary to perform sterilization treatment on the secondary tank before or after use of the dispensing device. However, in a case where the volume of the secondary tank is increased, the workability of the sterilization treatment decreases.

According to the dispensing device 100E of this embodiment, the secondary tank 21 is configured to include the first portion 211 and the second portion 212 which are separated from each other. In this way, it is possible to reduce the volume of each of the first portion 211 and the second portion 212 while securing the overall volume of the secondary tank 21. According to the dispensing device 100E of this embodiment, in the secondary tank 21, the portion in which the liquid is accommodated is the first portion 211. Therefore, in a case of performing sterilization treatment of the secondary tank 21, the sterilization treatment may be performed only on the first portion 211. Therefore, according to the dispensing device 100E of this embodiment, even though the overall volume of the secondary tank 21 is enlarged, it is possible to suppress a decrease in the workability of the sterilization treatment.

Seventh Embodiment

Figure 18:
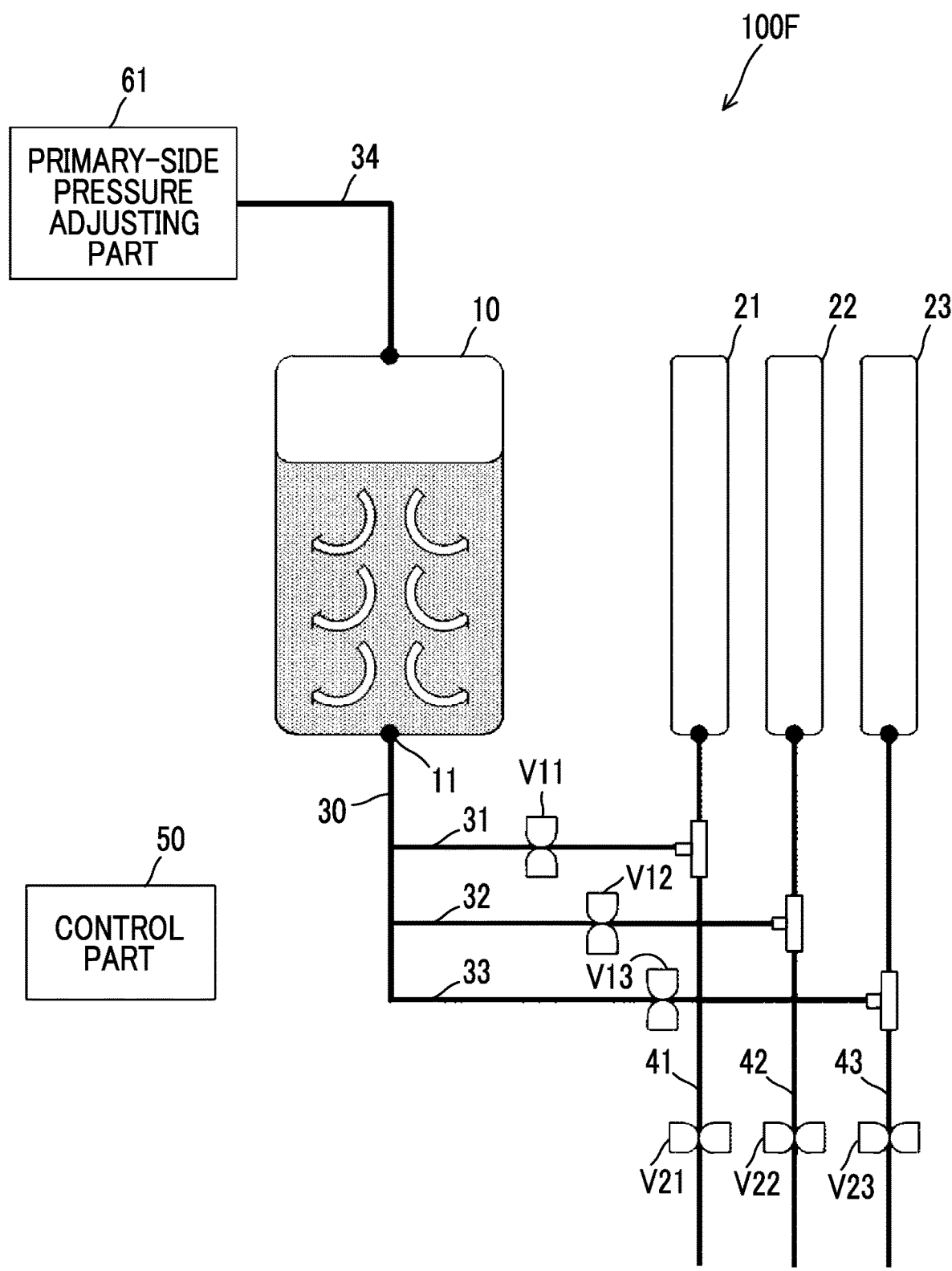
FIG. 18 is a diagram showing a configuration of a dispensing device according to another embodiment of the disclosed technique.

FIG. 18 is a diagram showing the configuration of a dispensing device 100F according to a seventh embodiment of the disclosed technique. The dispensing device 100F is different from the dispensing device 100 according to the first embodiment described above in that the primary tank 10 has a stirring function of stirring the liquid accommodated in the interior of the primary tank 10.

The stirring method is not particularly limited and, for example, the stirring may be performed by the rotation of a stirring blade provided in the interior of the primary tank 10. Further, the stirring may be performed by vibration or rocking of the primary tank 10. Further, the stirring may be performed by bubbling of the liquid accommodated in the interior of the primary tank 10. Further, the stirring may be performed by an operation of sucking up the liquid on the bottom surface side of the primary tank with a pump or the like and returning the sucked-up liquid into the primary tank again.

The primary tank 10 has a stirring function, whereby, for example, in a case where the liquid which is accommodated in the primary tank contains a plurality of fine particles, it becomes possible to substantially uniformly disperse the fine particles in the primary tank 10. Therefore, it becomes possible to transfer the liquid in which the fine particles are substantially uniformly dispersed from the primary tank 10 to each of the secondary tanks 21, 22, and 23, and thus in the liquid which is accommodated in each of the secondary tanks 21, 22, and 23, it is possible to make the density of the fine particles substantially uniform.

Further, the primary tank 10 has a stirring function, whereby, for example, in a case where the liquid which is accommodated in the primary tank contains a plurality of components, it becomes possible to substantially uniformly compound the plurality of components in the primary tank 10. Therefore, it becomes possible to transfer the liquid in which the plurality of components are substantially uniformly compounded from the primary tank 10 to each of the secondary tanks 21, 22, and 23, and thus it is possible to make the density ratio of the plurality of components substantially uniform in the liquid which is accommodated in each of the secondary tanks 21, 22, and 23.

Eighth Embodiment

Figure 19:
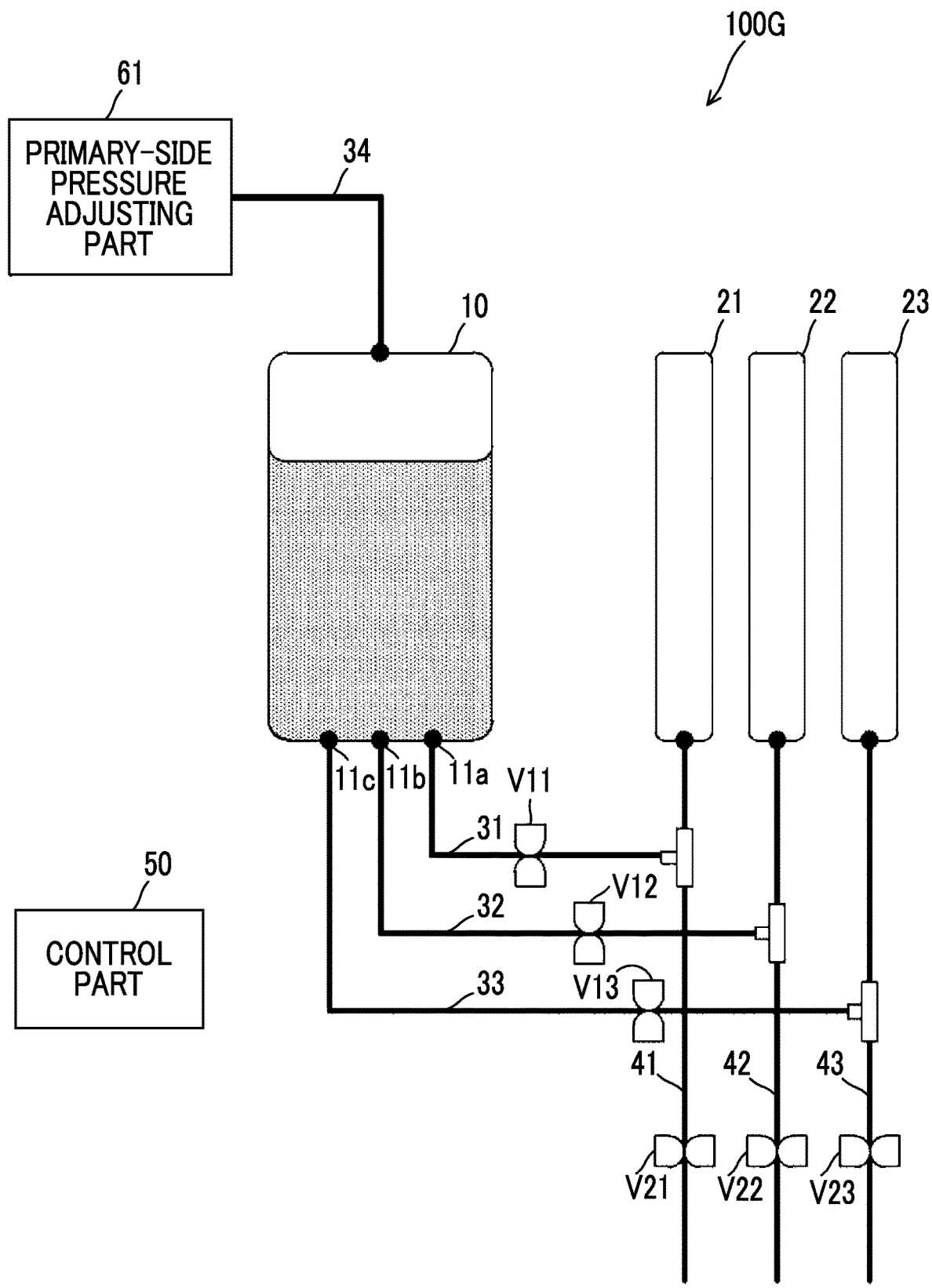
FIG. 19 is a diagram showing a configuration of a dispensing device according to another embodiment of the disclosed technique.

FIG. 19 is a diagram showing the configuration of a dispensing device 100G according to an eighth embodiment of the disclosed technique. The dispensing device 100G is different from the dispensing device 100 according to the first embodiment in that the primary tank 10 has a plurality of outflow ports 11a, 11b, and 11c provided in a bottom portion thereof. The outflow ports 11a, 11b, and 11c are respectively connected to the branch flow paths 31, 32, and 33.

That is, the branch portion for the liquid which is transferred from the primary tank 10 to each of the secondary tanks 21, 22, and 23 is provided at the primary-side discharge flow path 30 in the dispensing device 100 according to the first embodiment, whereas in the dispensing device 100D according to this embodiment, the branch portion is provided at the bottom portion of the primary tank 10.

Here, in a case where the liquid which is transferred from the primary tank 10 to each of the secondary tanks 21, 22, and 23 contains a plurality of fine particles, the density of the fine particles tends to become non-uniform between the branch destination flow paths in a case where the liquid is branched in a flow path having a small pipe diameter. Therefore, it is preferable to dispose the liquid branch portions in a relatively wide space.

According to the dispensing device 100G of this embodiment, the primary tank 10 has the plurality of outflow ports 11a, 11b, and 11c, and therefore, a configuration is made in which the branch portion for the liquid which is transferred from the primary tank 10 to each of the secondary tanks 21, 22, and 23 is disposed at the bottom portion of the primary tank 10. Therefore, as compared with a case where the branch portion for the liquid which is transferred from the primary tank 10 to each of the secondary tanks 21, 22, and 23 is provided at the primary-side discharge flow path 30, it becomes possible to enhance the uniformity of the density of the fine particles in the liquid which is accommodated in each of the secondary tanks 21, 22, and 23.

Figure 20:
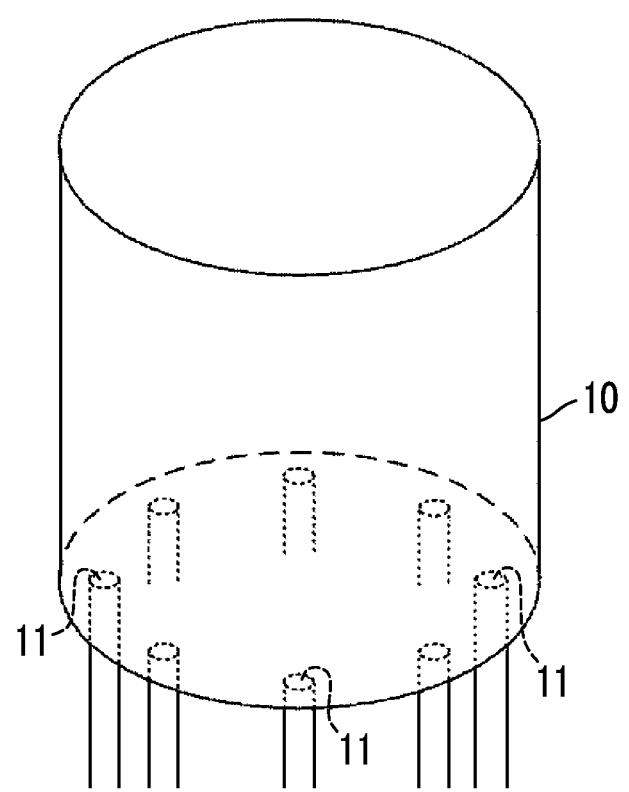
FIG. 20 is a perspective view showing a configuration of a primary tank according to another embodiment of the disclosed technique.

FIG. 20 is a perspective view showing an example of the configuration of the primary tank 10 having a plurality of outflow ports 11 at the bottom portion thereof. In the example shown in FIG. 20, the primary tank 10 has a columnar shape, and the plurality of outflow ports 11 are provided along the outer edge of the bottom surface thereof. Each of the plurality of outflow ports 11 is connected to the secondary tank through a branch flow path.

The constituent elements of the dispensing devices according to the first to eighth embodiments described above can be appropriately combined. For example, the first filter 63 and the second filter 64 of the dispensing device 100D according to the fifth embodiment may be applied to the dispensing devices according to the second to fourth embodiments. Further, the configuration of the secondary tank 21, the first filter 63, and the second filter 64 of the dispensing device 100E according to the sixth embodiment may be applied to the dispensing devices according to the second to fourth embodiments.

Further, the configuration of the primary tank 10 of the dispensing device 100F according to the seventh embodiment may be applied to the dispensing devices according to the first to sixth embodiments. Further, the configuration of the primary tank 10 of the dispensing device 100G according to the eighth embodiment may be applied to the dispensing devices according to the first to seventh embodiments.

Further, the lengths of the flow paths from the outflow port 11 of the primary tank 10 to the flow ports (21a, 21b, 21c) of the secondary tank, and the positions of the valves in the middle shown in FIGS. 1, 3 to 6, 8 to 10, 13, and 16 to 19 describing the first to eighth embodiments described above are described with different lengths for convenience of illustration. However, the length of the flow path and the position of the valve may be equivalent length and disposition in the respective flow paths.

The primary-side pressure adjusting part 61 and the control part 50 correspond to an example of primary-side pressure adjusting means in the disclosed technique. The secondary-side pressure adjusting part 62, the control part 50, and the pressure adjusting valves V24, V25, and V26 correspond to an example of secondary-side pressure adjusting means in the disclosed technique. The inflow-side valves V11, V12, and V13 correspond to an example of a first valve in the disclosed technique. The discharge-side valves V21, V22, and V23 correspond to an example of a second valve in the disclosed technique. The secondary-side discharge flow paths 41, 42, and 43 correspond to an example of a discharge flow path in the disclosed technique. The pressure sensors 81, 82, and 83 and the level sensors 91, 92, and 93 correspond to an example of a state detection part in the disclosed technique.

The entire disclosure of Japanese Patent Application No. 2017-015930 filed on Jan. 31, 2017 is incorporated in this specification by reference. Further, all the literatures, patent applications, and technical standards described in this specification are incorporated in this specification by reference to the same extent as a case where individual literature, patent application, and technical standard are specifically and individually stated to be incorporated by reference.

What is claimed is:

1. A dispensing device comprising:
a primary tank which accommodates a liquid;
primary-side pressure adjusting means for adjusting pressure in an interior of the primary tank;
a plurality of branch flow paths connected to the primary tank; and
a plurality of secondary tanks which are provided corresponding to the plurality of branch flow paths, respectively, and each of which is connected to a corresponding branch flow path,
wherein, in a state in which a gas in an interior of each of the plurality of secondary tanks is retained in the interior of each of the plurality of secondary tanks, the primary-side pressure adjusting means pressurizes an interior of the primary tank to transfer the liquid from the primary tank to each of the plurality of secondary tanks, the dispensing device further comprising:
secondary-side pressure adjusting means for adjusting pressure in the interior of each of the plurality of secondary tanks;
a first filter which suppresses inflow of unnecessary components contained in a gas which is supplied to the primary tank, into the interior of the primary tank in a case in which the primary-side pressure adjusting means pressurizes the interior of the primary tank; and
a second filter which suppresses inflow of unnecessary components contained in a gas which is supplied to each of the plurality of secondary tanks into the interior of each of the plurality of secondary tanks tank in a case in which the secondary-side pressure adjusting means pressurizes the interior of each of the plurality of secondary tanks,
wherein each of the plurality of secondary tanks includes a first subtank which accommodates the liquid which is transferred from the primary tank, and a second subtank which is connected to the first subtank through a connection pipe and has a flow port through which the gas which is accommodated in each of the plurality of secondary tanks, flows in a case in which the secondary-side pressure adjusting means pressurizes or depressurizes the interior of each of the plurality of secondary tanks, and
wherein the second filter is provided in the middle of the connection pipe.

2. The dispensing device according to claim 1,
wherein the secondary-side pressure adjusting means opens the interior of each of the plurality of secondary tanks to the atmosphere before the liquid transferred into the interior of each of the plurality of secondary tanks is discharged.

3. The dispensing device according to claim 1, further comprising:
a plurality of first valves each provided in the middle of each of the plurality of branch flow paths;
a plurality of discharge flow paths which are respectively connected to the plurality of secondary tanks, and through each of which the liquid which is discharged from each of the plurality of secondary tanks flows;
a plurality of second valves each provided in the middle of each of the plurality of discharge flow paths; and
a control part which controls each of the plurality of first valves to be in an open state and controls each of the plurality of second valves to be in a closed state, in a case of transferring the liquid from the primary tank to each of the plurality of secondary tanks, and controls each of the plurality of first valves to be in a closed state and controls each of the plurality of second valves to be in an open state, in a case of discharging the liquid accommodated in the interior of each of the plurality of secondary tanks from each of the plurality of secondary tanks.

4. The dispensing device according to claim 1,
wherein the primary tank has a plurality of outflow ports connected to the plurality of branch flow paths, respectively.

5. The dispensing device according to claim 1,
wherein volumes of the plurality of branch flow paths are equal to each other.

6. The dispensing device according to claim 1,
wherein the primary tank has a stirring function of stirring the liquid accommodated in the interior of the primary tank.

7. A liquid transfer method for transferring the liquid by using the dispensing device according to claim 1, the method comprising:
accommodating the liquid in the primary tank; and transferring the liquid from the primary tank to each of the plurality of secondary tanks by pressurizing the interior of the primary tank in a state where a gas in the interior of each of the plurality of secondary tanks is retained in the interior of each of the plurality of secondary tanks.

8. The dispensing device of claim 1, wherein for each of the plurality of secondary tanks, the first subtank, the second filter and the second subtank are connected in series via connection pipes between the primary tank and the secondary-side pressure adjusting means.

9. A dispensing device comprising:
a primary tank which accommodates a liquid;
primary-side pressure adjusting means for adjusting pressure in an interior of the primary tank;
a plurality of branch flow paths connected to the primary tank;
a plurality of secondary tanks which are provided corresponding to the plurality of branch flow paths, respectively, and each of which is connected to a corresponding branch flow path;
a state detection part which detects a state of an interior of at least one of the plurality of secondary tanks;
a plurality of valves each provided in the middle of each of the plurality of branch flow paths; and
a control part which controls opening and closing of each of the plurality of valves, based on a detection result of the state detection part,
wherein the state detection part includes a plurality of pressure sensors which are provided corresponding to the plurality of secondary tanks, respectively, and each of which detects pressure in an interior of a corresponding secondary tank, and
wherein the control part controls the valve, corresponding to the secondary tank, among the plurality of secondary tanks, in regarding to which it has been determined that the amount of accommodated liquid which is estimated from the pressure detected by the pressure sensor has reached a predetermined amount, to be in a closed state, in a case in which the liquid is transferred from the primary tank to each of the plurality of secondary tanks, the dispensing device further comprising:
secondary-side pressure adjusting means for adjusting the pressure in the interior of each of the plurality of secondary tanks, based on the pressure detected by each of the plurality of pressure sensors, in a case in which the liquid is transferred from the primary tank to each of the plurality of secondary tanks;
a first filter which suppresses inflow of unnecessary components contained in a gas which is supplied to the primary tank into the interior of the primary tank in a case in which the primary-side pressure adjusting means pressurizes the interior of the primary tank; and
a second filter which suppresses inflow of unnecessary components contained in a gas which is supplied to each of the plurality of secondary tanks, into the interior of each of the plurality of secondary tanks in a case in which the secondary-side pressure adjusting means pressurizes the interior of each of the plurality of secondary tanks,
wherein each of the plurality of secondary tanks includes a first subtank which accommodates the liquid which is transferred from the primary tank, and a second subtank which is connected to the first subtank through a connection pipe and has a flow port through which the gas which is accommodated in each of the plurality of secondary tanks flows in a case in which the secondary-side pressure adjusting means pressurizes or depressurizes the interior of each of the plurality of secondary tanks, and
wherein the second filter is provided in the middle of the connection pipe.

10. The dispensing device according to claim 9,
wherein the secondary-side pressure adjusting means decompresses the interior of each of the plurality of secondary tanks determined that the amount of accommodated liquid which is estimated from the pressure detected by the pressure sensor is smaller than a predetermined amount, among the plurality of secondary tanks, and pressurizes the interior of each of the plurality of secondary tanks determined that the amount of accommodated liquid which is estimated from the pressure detected by the pressure sensor is larger than the predetermined amount, among the plurality of secondary tanks, in a case where the liquid is transferred from the primary tank to each of the plurality of secondary tanks.

11. The dispensing device according to claim 9,
wherein in a state in which a gas in an interior of each of the plurality of secondary tanks is retained in the interior of each of the plurality of secondary tanks, the primary-side pressure adjusting means pressurizes an interior of the primary tank to transfer the liquid from the primary tank to each of the plurality of secondary tanks.

12. The dispensing device of claim 9, wherein for each of the plurality of secondary tanks, the first subtank, the second filter and the second subtank are connected in series via connection pipes between the primary tank and the secondary-side pressure adjusting means.

13. A dispensing device comprising,
a primary tank which accommodates a liquid;
primary-side pressure adjusting means for adjusting pressure in an interior of the primary tank;
a plurality of branch flow paths connected to the primary tank;
a plurality of secondary tanks which are provided corresponding to the plurality of branch flow paths, respectively, and each of which is connected to a corresponding branch flow path;
a state detection part which detects a state of an interior of at least one of the plurality of secondary tanks;
a plurality of valves each provided in the middle of each of the plurality of branch flow paths; and
a control part which controls opening and closing of each of the plurality of valves, based on a detection result of the state detection part,
wherein the state detection part includes a plurality of level sensors which are provided corresponding to the plurality of secondary tanks, respectively, and each of which detects a height of a liquid level of a liquid accommodated in an interior of a corresponding secondary tank, and
wherein the control part controls the valve corresponding to each of the plurality of secondary tanks, among the plurality of secondary tanks, in regarding to which it has been determined that the amount of accommodated liquid which is estimated from the height of the liquid level detected by the level sensor has reached a predetermined amount, to be in a closed state, in a case in which the liquid is transferred from the primary tank to each of the plurality of secondary tanks, the dispensing device further comprising:

secondary-side pressure adjusting means for adjusting the pressure in the interior of each of the plurality of secondary tanks, based on the height of the liquid level detected by each of the plurality of level sensors, in a case in which the liquid is transferred from the primary tank to each of the plurality of secondary tanks;

a first filter which suppresses inflow of unnecessary components contained in a gas which is supplied to the primary tank, into the interior of the primary tank in a case in which the primary-side pressure adjusting means pressurizes the interior of the primary tank; and a second filter which suppresses inflow of unnecessary components, contained in a gas which is supplied to each of the plurality of secondary tanks, into the interior of each of the plurality of secondary tanks in a case in which the secondary-side pressure adjusting means pressurizes the interior of each of the plurality of secondary tanks, wherein each of the plurality of secondary tanks includes a first subtank which accommodates the liquid which is transferred from the primary tank, and a second subtank which is connected to the first subtank through a connection pipe and has a flow port into through which the gas, which is accommodated in each of the plurality of secondary tanks flows in a case in which the secondary-side pressure adjusting means pressurizes or depressurizes the interior of each of the plurality of secondary tanks, and wherein the second filter is provided in the middle of the connection pipe.

14. The dispensing device according to claim 13, wherein the secondary-side pressure adjusting means decompresses the interior of each of the plurality of secondary tanks determined that the amount of accommodated liquid which is estimated from the height of the liquid level detected by the level sensor is smaller than a predetermined amount, among the plurality of secondary tanks, and pressurizes the interior of the secondary tank determined that the amount of accommodated liquid which is estimated from the height of the liquid level detected by the level sensor is larger than the predetermined amount, among the plurality of secondary tanks, in a case where the liquid is transferred from the primary tank to each of the plurality of secondary tanks.

15. The dispensing device of claim 13, wherein for each of the plurality of secondary tanks, the first subtank, the second filter and the second subtank are connected in series via connection pipes between the primary tank and the secondary-side pressure adjusting means.

* * * * *